United States Patent [19]
Murakami et al.

[11] 3,994,974
[45] Nov. 30, 1976

[54] α-AMINOMETHYLBENZYL ALCOHOL DERIVATIVES

[75] Inventors: Masuo Murakami; Kozo Takahashi; Toshiyasu Mase, all of Tokyo; Kiyoshi Murase; Hisashi Ida, both of Urawa, all of Japan

[73] Assignee: Yamanouchi Pharmaceutical Co., Ltd., Tokyo, Japan

[22] Filed: May 7, 1974

[21] Appl. No.: 468,009

Related U.S. Application Data

[63] Continuation-in-part of Ser. No. 325,596, Jan. 22, 1973, abandoned.

[30] Foreign Application Priority Data

Feb. 5, 1972 Japan................................ 47-13121
Apr. 19, 1972 Japan................................ 47-39416
May 23, 1972 Japan................................ 47-51013
May 27, 1972 Japan................................ 47-52925

[52] U.S. Cl........................... 260/562 A; 260/562 R; 260/562 P

[51] Int. Cl.² ........................................ C07C 103/38
[58] Field of Search ........ 260/562 A, 562 R, 562 P, 260/57.6

[56] References Cited
UNITED STATES PATENTS 2,393,820   1/1946   Schnider............................ 260/562
3,644,520   2/1972   Hartley et al....................... 260/562

OTHER PUBLICATIONS

Larsen et al., J. Med. Chem., vol. 10, pp. 462–472 (May 1967).
Burger, Medicinal Chem., 3rd Ed., Pt. II, pp. 1235–1286 (1970).

*Primary Examiner*—C. Davis
*Attorney, Agent, or Firm*—Burgess Ryan and Wayne

[57] ABSTRACT

Novel α-aminomethylbenzyl alcohol derivatives, particularly α-aminoethyl-3-substituted amino-4-hydroxybenzyl alcohol derivatives. The compounds of this invention are useful as bronchodilating agents.

4 Claims, No Drawings

α-AMINOMETHYLBENZYL ALCOHOL DERIVATIVES

This application is a Continuation-in-Part of pending application Ser. No. 325,596 filed Jan. 22, 1973 now abandoned.

DETAILED DESCRIPTION OF THE INVENTION

The present invention relates generally to novel α-aminomethylbenzyl alcohol derivatives and more particularly, it relates to novel α-aminomethylbenzyl alcohol derivatives represented by the general formula I

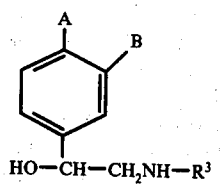

wherein one of A and B represents a hydrogen atom or a hydroxyl group while the other of them represents a

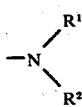

group (in which $R^1$, which is different from $R^2$, represents a hydrogen atom or an alkyl group having 1 to 7 carbon atoms and $R^2$ represents a hydrogen atom or a —CO—$R^4$ group in which $R^4$ represents a hydrogen atom, a hydroxyalkyl group having 1 to 7 carbon atoms or an alkanoylaminoalkyl group having 2 to 10 carbon atoms) and $R^3$ represents an alkyl group having 3 to 7 carbon atoms, a cycloalkylalkyl group having 6 to 12 carbon atoms or

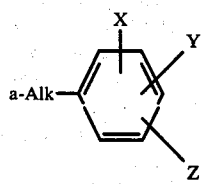

group (wherein Alk represents a straight or branched alkylene group having 1 to 7 carbon atoms, and X, Y and Z are the same of different from each other and each represents a hydrogen atom, a hydroxy group, an alkanoylamino group having 1 to 7 carbon atoms, an alkyl group having 1 to 7 carbon atoms or an alkoxy group having 1 to 7 carbon atoms).

The compounds of this invention have utility as β-adrenergic stimulants and thus have great activity on respiratory smooth muscle and are suitable as bronchodilating agents.

As a compound having bronchodilating effects, there are known hitherto various compounds and especially, Isoproterenol and Trimetoquinol, these compounds being well known among the bronchodilating drugs and being widely sold since they have strong effects. Further a bronchlodilating agent should not have any ill-effects on the heart that is, it should have high selectivity, and Salbutamol satisfies this requirement and is also widely sold.

Further, compounds having a similar structure to the present compounds are the known 3-amino-4-hydroxy-α-isopropylaminomethylbenzyl alcohol (see Dutch Patent No. 85197: "Chemical Abstract", 52 11121d (1958)), 3-ethoxycarbonylamino-4-hydroxy-α-isopropylaminomethylbenzyl alcohol (see Belgian Patent No. 765,986), α-(isopropylaminomethyl)-4-hydroxy-3-ureido benzyl alcohol (see Japanese Patent Application Public Open No. 2676/1971).

As a result of various investigations in this area, the present inventors have discovered that the novel α-aminomethylbenzyl alcohols represented by the formula (I) supra have superior bronchodilating effects and are superior bronchodilating agents having a high selectivity.

In formula I representing the compounds of this invention, examples of $R^1$ are a hydrogen atom, an alkyl group such as a methyl group, an ethyl group, a propyl group, an isopropyl group, a n-butyl group, a tert butyl group, a 1, 3-dimethylbutyl group, a 1, 3-dimethylpentyl group, a 2, 3-dimethylbutyl group, a 2, 3, 3-tributyl group, etc.; examples of $R^4$ are a hydrogen atom, a hydroxyalkyl group such as a hydroxymethyl group, a hydroxyethyl group, a hydroxypropyl group, a hydroxybutyl group, etc., an alkanoylaminoalkyl group such as a formamidemethyl group, an acetylaminomethyl group, an acetylaminoethyl group, an acetylaminopropyl group, a butyrylaminoethyl group, etc. Examples of an alkyl group of $R^3$ are a propyl group, an isopropyl group, a n-butyl group, a tert-butyl group, a 1, 3-dimethylbutyl group, a 1, 3-dimethylpentyl group, a 2, 3-dimethylbutyl group, a 2, 3, 3-trimethylbutyl group, etc.; examples of the cycloalkyl group of $R^3$ are a cyclopentylmethyl group, a 2-cycloethyl group, a cyclohexylmethyl group, a 2-cyclohexylethyl group, a 3-cyclohexyl-1-methylpropyl group, etc. Examples of Alk are an alkylene group such as methylene group, an ethylene group, a propylene group, a butylene group, a 1-methylethylene group, a 1-ethylethylene group, a 1-methylpropylene group, a 1-ethylpropylene group, a 2-methylpropylene group, a 3-methylbutylene group, a 2-ethylbutylene group, etc. The examples of X, Y and Z are a hydrogen atom, a hydroxy group, al alkanoylamino group such as a formamide group, an acetylamino group, a propionylamino group, a butyrylamino group, etc., an alkyl group such as a methyl group, an ethyl group, a propionyl group, an isopropyl group, an isobutyl group, a tert-butyl group, etc., or an alkoxy group such as a methoxy group, an ethoxy group, a propoxy group, an isopropoxy group, a butoxy group, etc.

The particularly useful compounds of this invention are 3-formamido-4-hydroxy-α-[N-(1-methyl-2-p-hydroxyphenylethyl) amino-methyl] benzyl alcohol, 3-formamido-4-hydroxy-α-[N-(1-methyl-2-p-methoxyphenylethyl) aminomethyl]benzyl alcohol, 4-hydroxy-3-methylamino-α-(N-tert-butylaminomethyl) benzyl alcohol, etc.

When A of the formula I representing the compounds of this invention is a hydroxyl group and B is the

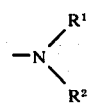

group, the compounds of this invention are shown by the formula I'

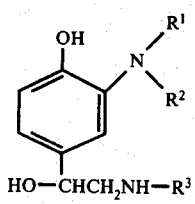

wherein R¹, R², and R³ have the same significance as in the formula I and more specifically the formula I' includes the following three formulae;

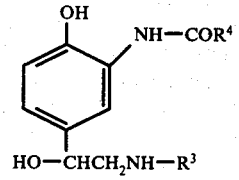

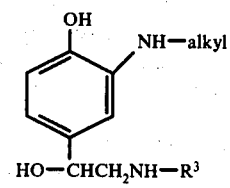

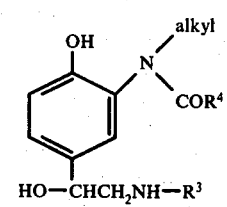

in the above formulae, R³ and R⁴ have the same significance as in formula I.

As the starting materials for preparing the products of this invention, there are used those compounds wherein one or more of hydrogen atoms of the monosubstituted amino group and the hydroxyl group thereof have been protected by a group capable of being easily released by reduction, such as a benzyl group, a benzyloxycarbonyl group, a p-nitrobenzyloxycarbonyl group, etc.

Furthermore, the starting materials for the products of this invention which have a hydroxyl group bonded to the benzene ring through a =CH-group, i.e., a secondary hydroxyl group, may be a compound having a carbonyl group at the position

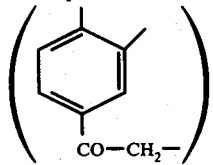

The compounds of this invention may be prepared by catalytic reduction, e.g., the starting materials or salts thereof in a solvent such as ethanol, isopropanol, ethyl acetate, and the like, at normal temperature or an elevated temperature, under a normal pressure or a high pressure, in the presence of a catalyst such as palladium, platinum, and the like, according to conventional procedures.

Suitable starting materials for the compounds of this invention are as follows:

3-formamido-4-benzyloxy-α-(N-benzyl-N-isopropylaminomethyl)-benzyl alcohol,
3-formamido-4-benzyloxy-α-(3-p-hydroxyphenyl-1-methylpropylamino) acetophenone,
3-benzyloxyacetamido-4-hydroxy-α-[N-benzyl-N-(1-ethyl-2-p-methoxyphenylpropyl) amino] acetophenone,
3-(3-benzyloxypropionamido)-4-benzyloxycarbonyloxy-α-[N-(1-methyl-2-m-acetamidophenyl) amino] acetophenone,
3-(2-acetamidopropoamido)-4-hydroxy-α[N-benzyl-N-(1-methyl-3-o-tolylpropyl) amino] acetophenone,
3-butyrylamino-4-hydroxy-α-[N-(o-methyl-m-ethoxyphentlpropyl) amino] acetophenone,
3-formylamino-4-benzyloxy-α-[N-benzyl-N-1,1-dimethyl-2-p-hydroxyphenylethyl) aminomethyl]-benzyl alcohol,
3-formamido-4-hydroxy-α-[N-benzyl-N-(1-ethyl-2-p-hydroxyphenylethyl) aminomethyl]benzyl alcohol,
3-formadmido-4-benzyloxy-α-[N-benzyl-N-(1-methyl-2-p-acetamidophenylethyl) aminomethyl]benzyl alcohol,
3-benzyloxyacetamido-4-hydroxy-α-[N-benzyl-N-(1-methyl-2-p-propoxyphenylethyl)amino]acetophenone,
3-acetamidopropioamido-4-benzyloxy-α-[N-benzyl-N-(1-methyl-2-p-ethoxyphenylethyl)aminomethyl]benzyl alcohol,
3-formamido-α-(N-benzyl-N-isopropylaminomethyl) benzyl alcohol,
3-formamido-α-(N-benzyl-N-tert-butylaminomethyl) acetophenone.

When the hydroxyl groups of the groups R³ and R⁴ of those starting materials for the compounds of this invention have been substituted by benzyl groups, benzyloxycarbonyl groups, etc., the substituents of the hydroxyl groups are released to give the hydroxyl groups at the practice of the aforesaid reduction.

The desired products of formula I thus obtained can be isolated and purified by an ordinary chemical operation. Furthermore, because the compounds represented by formula I of this invention have at least one asymmetric carbon atom, the compounds of this invention include all the possible optical active forms and racemic mixtures. The racemic mixture may be resolved by such a known method as, for example, forming optically active acid addition salts and then separating them by fractional crystallization.

The pharmacological effects of the compounds of this invention will be illustrated in the following experiments and results while comparing these of known compounds.

EXPERIMENT I

Activity on isolated bronchial smooth muscle (in vitro test)

The trachea of a guinea pig was cut spirally and the isolated bronchial preparation was suspended in Magnus bath. Tyrode's solution was filled in a 50 ml bath and kept at 37° C. Then, $10^{-5}$ g/ml of histamine dihydrochloride or methacholine chloride was added to a bath as spasmogen. After the contraction of the trachea reached a plateau, a test substance shown in the below-showing table was added to the preparation, cumulatively. The concentration producing 50% relaxation of the contracted bronchial muscle was designated as $ED_{50}$. The results are shown in the Table I.

Table I

| Sample | Anti-histamine ED$_{50}$ (g/ml) | Anti-histamine relative activity | Anti-methacholine Chloride ED$_{50}$ (g/ml) | Anti-methacholine Chloride relative activity |
| --- | --- | --- | --- | --- |
| 3-acetylamino-4-hydroxy-α-(isopropylaminomethyl)benzyl alcohol hydrochloride (compared compound) | $1 \times 10^{-6}$ | 370 | $>10^{-4}$ | $>4760$ |
| 3-formylamino-4-hydroxy-α-[N-(1-methyl-2-p-hydroxyphenyl-ethyl)aminomethyl]benzyl alcohol [A].½ fumarate (compound of Example 8) | $9.4 \times 10^{-10}$ | 0.35 | $1.1 \times 10^{-8}$ | 0.52 |
| 3-formylamino-4-hydroxy-α-[N-(1-methyl-3-p-hydroxyphenyl-propyl)aminomethyl]benzyl alcohol. ½ fumarate monohydrate (compound of Example 19) | $8.6 \times 10^{-10}$ | 0.32 | $8.9 \times 10^{-9}$ | 0.42 |
| 3-formylamino-4-hydroxy-α-[N-(1-methyl-2-p-methoxyphenyl-ethyl)-aminomethyl]benzyl alcohol [A] ½ fumarate (compound of Example 22) | $4.6 \times 10^{-10}$ | 0.17 | $4.6 \times 10^{-9}$ | 0.22 |
| Known compounds | | | | |
| A | $3 \times 10^{-7}$ | 111 | $3 \times 10^{-6}$ | 143 |
| B | $5 \times 10^{-6}$ | 185 | $>10^{-4}$ | $>4760$ |
| C | $9 \times 10^{-8}$ | 3.33 | $>10^{-4}$ | $>4760$ |
| D | $1 \times 10^{-8}$ | 3.7 | $9.6 \times 10^{-8}$ | 4.57 |
| E* | $2.7 \times 10^{-9}$ | 1.0 | $2.1 \times 10^{-8}$ | 1.0 |
| F | $5.5 \times 10^{-9}$ | 2.04 | $2.8 \times 10^{-8}$ | 1.33 |

*control

Known compounds used above are as follows:
A: 3-amino-4-hydroxy-α-isopropylaminomethylbenzyl alcohol (Dutch Patent No. 85,197).
B: 3-ethoxycarbonylamino-4-hydroxy-α-isopropylaminomethylbenzyl alcohol (Belgian Patent No. 765.986)
C: 4-hydroxy-3-(N'-methylureido)-α-isopropylaminomethylbenzyl alcohol (Japanese Patent Application Public Open No. 2674/'71)
D: Salbutamol; 4-hydroxy-3-hydroxymethyl-α-tert-butylaminomethylbenzyl alcohol
E: Trimetoquinol; 1-1-(3,4,5-trimethoxybenzyl)-6,7-dihydroxy 1,2,3,4-tetrahydroisoquinoline hydrochloride
F: Isoproterenol; α-(isopropylaminomethyl) protocatechuyl alcohol

EXPERIMENT II

Activity on experimental asthma (in vivo test)

A guinea pig was placed in a 11 liter glass chamber and exposed to the spasmogen by means of a nebulizer. Thus, when 0.01% histamine dihydrochloride or methacholine chloride solution was sprayed into a chamber for 10 seconds, the guinea pigs showed the symptoms of dyspnea. Drugs were administered subcutaneously to animals 30 minutes before application of the spasmogen. If a guinea pig showed no asthmatic dyspnoic symptoms, the drug was evaluated to be effective. ED$_{50}$ was calculated by the method of Litchfield-Wilcoxon [J. Pharmacol. Exptl. Therap, 96, 99–113 (1949)]. The results are shown in Table II.

Table II

| Sample | Histamine-asthma ED$_{50}$ (μg/Kg) | Methacholine chloride-asthma Ed$_{50}$ (μg/Kg) |
| --- | --- | --- |
| 3-formylamino-4-hydroxy-α-[N-(1-methyl-2-p-hydroxyphenyl-ethyl)aminomethyl]benzyl alcohol [A]. ½ fumarate (compound of Example 8) | 1.9 | 2.6 |
| 3-formylamino-4-hydroxy-α-[N-(1-methyl-3-p-hydroxyphenyl-propyl)aminoethyl]benzyl alcohol ½ fumarate. monohydrate (compound of Example 19) | 1.4 | 8.1 |
| 3-formylamino-4-hydroxy-α-[N-(1-methyl-2-p-methoxyphenylethyl)-aminomethyl]benzyl alcohol [A]. ½ fumarate (compound of Example 22) | 3.6 | — |
| Known compounds | | |
| E | 11.3 | 12.4 |
| F | 15.7 | 11.2 |

EXPERIMENT III

Mongrel dogs of either sex weighing about 10 Kg were anesthetized with pentobarbital Na, 35 mg/Kg intravenously, and prepared for measurement of bronchial resistance (Konzett & Roessler; Arch exp. Path. Pharmakol, 195, 71–74 (1940)). Temporary increases in bronchial resistance, measured with a low pressure transducer connected to a penrecorder, were produced by histamine dihydrochloride 10 μg/Kg injected intravenously at intervals of 10 minutes. The test samples were injected intravenously 5 minutes before injection of histamine, cumulatively. In all experiments, the drugs were injected intravenously through a cannula in a femoral vein. $ED_{50}$ values of β-agonists were obtained from the dose-response (inhibition) curves. ($β_2$- action).

Mongrel dogs of either sex weighing about 10 Kg were anesthetized with pentobarbital Na, 30 mg/Kg intravenously. Arterial blood pressure was measured from a cannula in the right femoral artery and the pulse pressure used to trigger a ratemeter for a record of heart rate. ($β_1$.action). Intravenous injections were made through a cannula in a femoral vein, and $ED_{50bpm}$ values were obtained from the does-response (ΔHR) curves. $ED_{50bpm}$ vs. $ED_{50}$ ratios mean its own selectivity.

Table III

| Sample | $β_2$-action $ED_{50}$ (μg/Kg) | $β_1$-action $ED_{50bpm}$ (μg/Kg) | Selectivity (ratio of $β_1/β_2$ |
|---|---|---|---|
| 3-formylamino-4-hydroxy-α-[N-(1-methyl-2-p-hydroxyphenylmethyl)aminomethyl]-benzyl alcohol [A]. ½ fumarate (compound of Example 8) | 0.031 | 0.26 | 8.38 |
| 3-formylamino-4-hydroxy-α-[N-(1-methyl-3-p-hydroxyphenylpropyl)aminomethyl]-benzyl alcohol. ½ fumarate. monohydrate (compound of Example 19) | 0.050 | 0.59 | 12 |
| 3-formylamino-4-hydroxy-α-[N-(1-methyl-2-p-methoxyphenylmethyl)aminomethyl] benzyl alcohol [A]. ½ fumarate (compound of Example 22) | 0.038 | 0.72 | 18.9 |
| Known compound D | 1.4 | 7.0 | 5.0 |

As shown in Table I, the activity on bronchial smooth muscle of the present products is greater than that of the compounds A, B or C each having the similar structure to the instant compound, or Trimetoquinol (E) or Isoproterenol (F), since $ED_{50}$ values of the present compounds are smaller than that of said each compounds.

As shown in Table II, the antiasthmatic action of the present compounds in vitro is greater than that of Trimetoquinol (E) or Isoproterenol (F) each being well known for their strong effects among the bronchodilating drugs being widely sold, since $ED_{50}$ of the present compounds are less than that of compounds E or F.

As shown in Table III, the present products are more selective than that of Salbutamol (D) having high selectivity, since the ratio of $β_1/β_2$ of the present compounds is greater than that of Salbutamol (D).

For the above reasons, it is clear that the present products have superior bronchodilating activity and further they are superior bronchodilating agents having a high selectivity as compared with known bronchodilators.

The products of this invention may be used in various forms and in general they are used in the form of the salts of pharmacologically useful nontoxic acids. For example, they are used as the salts of such inorganic acids as hydrochloric acid, sulfuric acid, phosphoric acid, and the like, or such organic acids as fumaric acid, maleic acid, acetic acid, lactic acid, citric acid, and the like.

The compounds of this invention may be administered orally or parenterally. In the case of oral administration, they may be in the form of sugar-coated tablets, buccals, or capsules. They may also be in the form of aerosols as inhalations. Furthermore, they may be injected subcutaneously, intramuscularly, or intravenously as injections.

The dosage of the compounds of this invention depends upon the condition of the patients, their ages, and administration form but the suitable oral dosage range for an adult is 0.3–1.5 mg./day.

REFERENCE EXAMPLE 1.

a. In 60 ml. of chloroform was dissolved 5.4 g. of 4-benzyloxy-3-nitroacetophenone and after dropwise to the solution a mixture of 3.2 g. of bromine and 5 ml. of chloroform with stirring, the mixture was stirred further for 30 minutes. The reaction product was concentrated under a reduced pressure and the crystalline residue obtained was washed with 20 ml. of benzene and dried to give 5.5 g. of 4-benzyloxy-3-nitro-α-bromoacetophenone. The product, when recrystallized from chloroform, melted at 135°–136° C.

b. In 60 ml. of tetrahydrofuran was dissolved 5.3 g. of 4-benzyloxy-3-nitro-α-bromoacetophenone and after adding to the solution 4.5 g. of N-benzyl-N-isopropylamine, the mixture was stirred overnight at room temperature. Then, after filtering off the precipitates thus formed, the filtrate was concentrated under a reduced pressure and the crystalline residue obtained was washed with ethanol to provide 5.5 g. of the yellow crystal line 4-benzyloxy-3-nitro-α-(N-benzyl-N-isopropylamino) acetophenone. The product, when recrystallized from ethanol, melted at 92°–93° C.

c. In 35 ml. of ethanol was suspended 3.5 g. of 4-benzyl-oxy-3-nitro-α-(N-benzyl-N-iso-propylamino)acetophenone and after adding to the suspension 0.4 g. of sodium borohydride, the mixture was stirred for 3 hours at room temperature. After distilling off ethanol from the reaction product under a reduced pressure and adding water to the residue, the product was extracted with benzene. The extract was washed with water, dried over anhydrous magnesium sulfate, and then concentrated under a reduced pressure to provide 3.4 g. of faint-yellow crystals of 4-benzyloxy-3-nitro-α-(n-benzyl-N-isopropylaminomethyl)-benzyl alcohol. The product, when recrystallized from ethanol, melted at 97° C.

d. In 30 ml. of 50% aqueous acetic acid solution was dissolved 3 g. of 4-bensyloxy-3-nitro-α-(N-benzyl-N-isopropylaminomethyl) benzyl alcohol and after adding to the solution 1.5 g. or iron powder, the mixture was refluxed for 30 minutes under heating. After filtering off the insoluble materials from the reaction product, the filtrate was concentrated under a reduced pressure. To the residue thus obtained was added 20 ml. of 5% aqueous sodium carbonate solution and the product was extracted with benzene. The extract was washed with water, dried over anhydrous magnesium sulfate, and concentrated under a reduced pressure to provide the brownish crystal of 3-amino-4-benzyloxy-α-(N-benxyl-N-isopropylaminomethyl)-benzyl alcohol.

The product, when recrystallized from 2:5 benzene-n-hexane, melted at 63°–65° C. The amount of the product obtained was 2.2 g.

e. In 5 ml. of a mixture of acetic anhydride and formic acid was dissolved 1.9 g. of 3-amino-4-benzyloxy-α-(N-benzyl-N-isopropylaminomethyl) benzyl alcohol and after allowing this mixture to stand overnight, the solution was concentrated under a reduced pressure. After adding to the residue thus obtained 20 ml. of 5% aqueous sodium carbonate solution, the product was extracted with 30 ml. of benzene. The extract was washed with water, dried over anhydrous magnesium sulfate, and concentrated under a reduced pressure to provide 1.9 g. of a brownish oily 4-benzyloxy-3-formylamino-α-(N-benzyl-N-isopropylaminomethyl) benzyl alcohol.

The product was dissolved in 10 ml. of 90% methanol and after adding to the solution 0.5 g. of sodium carbonate, the mixture was stirred for 30 minutes at room temperature. Then, the solvent was distilled off under a reduced pressure and the residue obtained was extracted with benzene. The extract was washed with water, dried over anhydrous magnesium sulfate, and concentrated under a reduced pressure to provide 1.9 g. of a brownish oily 4-benzyloxy-3-formylamino- -(N-benzyl-N-isopropylaminomethyl)benzyl alcohol.

REFERENCE EXAMPLE 2.

a. In 30 ml. of pyridine was dissolved 5 g. of 3-amino-4-benzyloxyacetophenone and after adding to the solution 3.9 g of benzyloxyacetyl chloride under cooling, the mixture was stirred overnight at room temperature. The solvent was distilled off from the reaction product under a reduced pressure, the residue formed was dissolved in 50 ml. of chloroform, and then the solution was washed twice each time with 20 ml. of water. Then, the solution was dried over anhydrous sodium sulfate and chloroform was distilled off under a reduced pressure. By recrystallizing the yellow crystals thus obtained from ethanol, 7.5 g. of 4-benzyloxy-3-benzyloxyacetylamino-acetophenone melting at 104°–105° C was obtained.

b. In 50 ml. of chloroform was dissolved 1.9 g. of 4-benzyloxy-3-benzyloxyacetylaminoacetophenone and after adding to the solution 0.78 g. of bromine, the mixture was stirred for 30 minutes at room temperature. Then, chloroform and hydrogen bromide were distilled off from the reaction mixture under a reduced pressure and the crystal material thus obtained was recrystallized from chloroform-n-hexane to provide 1.85 g. of 4-benzyloxy-3-benzyloxy-acetylamino-α-bromoacetophenone melting at 155°–157° C.

c. In 100 ml. of tetrahydrofuran was dissolved 4 g. of 4-benzyloxy-3-benzyloxyacetylamino-α-bromoacetophenone at 40°–50° C. and after adding to the solution 2.68 g. of N-benzyl-N-sopropylamine, the mixture was stirred overnight at the same temperature as above. The reaction product was cooled, N-benzyl-N-isopropylamine hydrochloride formed was filtered off and then the solvent was distilled off under a reduced pressure. After dissolving the yellow oily material (5 g.) thus obtained in 100 ml. of ethanol, 0.5 g. of sodium borohydride was added to the solution and the mixture was stirred for 4 hours at room temperature. Then, the solvent was distilled off from the reaction product under a reduced pressure and the white crystals thus obtained were recrystallized from ethanol to give 2.3 g. of 4-benzyloxy-3-benzyloxyacetylamino-α-(N-benzyl-J-isopropylaminomethyl) benzyl alcohol melting at 93°–95° C.

REFERENCE EXAMPLE 3.

a. In 50 ml. of chloroform was dissolved 5.4 g. of 4-hydroxy-3-nitroacetophenone and then 5 ml. of chloroform solution of 4.8 g. of bromine was added dropwise to the solution gradually. Thereafter, the mixture was stirred for 15 minutes and concentrated under a reduced pressure to form yellow crystals. By recrystallizing the product from benzene-n-hexane, 6.3 g. of the crystals of α-bromo-4-hydroxy-3-nitroacetophenone melting at 69°–71° C. were obtained.

b. In 50 ml. of methyl ethyl ketone was dissolved 5.2 g. of α-bromo-4-hydroxy-3-nitroacetophenone and after adding to the solution 9 g. of N-benzylisopropylamine, the mixture was stirred overnight at room temperature. After filtering off the hydrobromide of N-benzylisopropylamine thus precipitated, the filtrate was concentrated to provide a crude yellowish brown oily 4-hydroxy-3-nitro-α-(N-benzyl-N-isopropylamino) acetophenone.

c. In 50 ml. of ethanol was dissolved the crude 4-hydroxy-3-nitro-α-(N-benzyl-N-isopropylamino) acetophenone prepared above and after adding to the solution 1.5 g. of sodium borohydride, the mixture was stirred overnight at room temperature. The reaction product was concentrated under a reduced pressure and after adding water to the residue thus obtained, the product was extracted with benzene. The extract was washed with water, dried over anhydrous magnesium sulfate, and then the solvent was distilled off to give a yellow-brown oily material. The oily product was subjected to a silica gel column chromatography, the product was then recovered therefrom using benzene as an eluting agent, and from the effluents collected there was obtained 4 g. of 4-hydroxy-3-nitro-α-(N-benzyl-N-isopropylamino-methyl) benzyl alcohol.

d. In 30 ml. of methanol was dissolved 2.7 g. of the 4-hydroxy-3-nitro-α-(N-benzyl-N-isopropylamino-ethyl) benzyl alcohol prepared above and after adding to the solution 1 g. of Raney nickel catalyst, the catalytic reduction of the compound was conducted at normal temperature and normal pressure. When 600 ml. of hydrogen was absorbed, the reaction was stopped. After filtering off the catalyst and adding 8.2 ml of 1 normal hydrogen chloride-ethanol solution to the filtrate, the reaction product was concentrated under a reduced pressure to provide 2.7 g. of a yellow-brown powder of 3-amino-4-hydroxy-α-(N-benzyl-N-isopropylaminomethyl) - benzyl alcohol hydrochloride.

e. In 20 ml. of pyridine was dissolved 1.2 g. of the 3-amino-4-hydroxy-α-(N-benzyl-N-iso-propylaminomethyl) benzyl alcohol hydrochloride prepared above and after adding to the solution 0.20 g. of formic acid and 0.85 g. of dicyclohexylcarbodiimide under cooling below 0° C., the mixture was stirred overnight at room temperature. The dicyclohexyl urea thus precipitated was filtered off, the filtrate was concentrated, and after adding water to the residue, the mixture was washed with ethyl acetate. The aqueous solution formed was neutralized by the addition of sodium carbonate and then extracted with ethyl acetate. The extract was dried and concentrated to give a brown residue. The residue was subjected to a silica gel column chromatography, the product was recovered using a 5 : 1 chloroform-acetone mixture as an eluting agent, and then from the effluents there was obtained 0.5 g. of a yellow powder of 3-formylamino-4-hydroxy-α-(N-benzyl-N-isopropylaminomethyl) benzyl alcohol.

REFERENCE EXAMPLE 4 a. In 60 ml of chloroform there was dissolved 5.4 g of 4-benzyloxy-3-nitroacetophenone and after adding dropwise to the solution a mixture of 3.2 g of bromine and 5 ml. of chloroform, with stirring, the mixture was further stirred for 30 minutes. The reaction product was concentrated under a reduced pressure and the crystalline residue thus obtained was washed with 20 ml. of benzene and dried to give 5.5 g of 4-benzyloxy-3-nitro-α-bromoacetophenone melting at 135°–136° C.

b. A mixture of 4.6 g of 4-benzyloxy-3-nitro-α-bromoacetophenone and 6.4 g of N-benzyl-N-(1-methyl-2-p-hydroxyphenylethyl) amine was heated together with 50 ml. of methyl ethyl ketone to 70°–80° C for 30 minutes.

After cooling the reaction product, the precipitates formed were filtered off and the filtrate was concentrated under a reduced pressure. When ethanol was added to the residue obtained, the product was crystallized. The crystalline material was recovered by filtration and recrystallized from ethanol to provide 5.5 g of 4-benzyloxy-3-nitro-α-[N-benzyl-N-(1-methyl-2-p-hydroxyphenylethyl)amino]-acetophenone melting at 84°–85° C.

c. In 100 ml. of ethanol there was suspended 4.5 g of 4-benzyloxy-3-nitro-α-[N-benzyl-N-(1-methyl-2-p-hydroxyphenylethyl)-amino] acetophenone and after adding to the suspension 0.5 g of sodium borohydride, the mixture was stirred for one hour at room temperature. Then, ethanol was distilled off from the reaction product under reduced pressure and after adding water to the residue, the product was extracted with benzene. The extract was washed with water, dried over anhydrous magnesium sulfate, and then concentrated under reduced pressure to give the 4.4 g of a yellowish crystalline powder of 4-benzyloxy-3-nitro-α-[N-benzyl-N-(1-methyl-2-p-hydroxyphenylethyl) aminomethyl] benzyl alcohol.

d. In 40 ml. of a 60% aqueous acetic acid solution there was dissolved 4.3 g. of 4-benzyloxy-3-nitro-α-[N-benzyl-N-(1-methyl-2-p-hydroxyphenylethyl)aminomethyl] benzyl alcohol and after adding to the solution 1.5 g. of iron powder, the mixture was refluxed for 30 minutes under heating. After filtering off the insoluble material from the reaction product, the product was concentrated under a reduced pressure. To the residue obtained there was added a 10% aqueous sodium carbonate solution and the product was extracted with benzene. The extract was washed with water, dried over anhydrous magnesium sulfate, and concentrated under a reduced pressure to give 3.7 g. of a brownish crystalline powder of 3-amino-4-benzyloxy-α-[N-benzyl-N-(1-methyl-2-p-hydroxyphenylethyl) aminomethyl] benzyl alcohol.

e. In 10 ml. of a 5 : 3 acetic anhydride formic acid mixture was dissolved 3.3 g. of 3-amino-4-benzyloxy-α-[N-benzyl-N-(1-methyl-2-p-hydroxyphenylethyl)aminomethyl] benzyl alcohol and after allowing the mixture to stand overnight at room temperature, the mixture was concentrated under reduced pressure. The residue thus obtained was dissolved in 50 ml. of methanol and after adding to the solution 3 ml. of water and 3 g. of sodium carbonate, the mixture was stirred for one hour at room temperature. Methaol was distilled off under reduced pressure from the mixture and the residue was extracted with ethyl acetate. The extract was washed with water, dried over anhydrous magnesium sulfate, and the solvent was distilled off from the extract to give 3.4 g. of a faint-brown powder of 4-benzyloxy-3-formylamino-α-[N-benzyl-N-(1-methyl-2-p-hydroxyphenylethyl) amino-methyl] benzyl alcohol. In 30 ml. of benzene there was dissolved 2.5 g. of the faint brown powder obtained above and on allowing the solution to stand overnight at room temperature, crystals were formed. The crystals were separated and recrystallized from ethyl acetate-benzene to give 1.2 g. of a white crystalline material melting at 135°–137° C.

Nuclear magnetic resonance spectra: ($CDCl_3$)

δ: 4.50 ppm. (m, 1H, CH at the root of hydroxyl group), 3.46, 3.87 ppm. (AB pattern, q, $2H,CH_2$ at the root of N).

This product is called 4-benzyloxy-3-formylamino-α-[N-benzyl-N-(1-methyl-2-p-hydroxyphenylethyl)aminomethyl] benzyl alcohol [A].

Furthermore, the solvent was distilled off from the mother liquor left in the above step and the residue thus obtained was subjected to a silica gel column chromatography. Then, by using 10 : 2 benzene ethyl acetate mixture, 0.8 g. of a white crystalline powder was obtained.

Nuclear magnetic resonance spectra: ($CDCl_3$)

δ: 4.34 ppm (m, 1H, CH at the root of hydroxyl group), 3.76 ppm. (S, 2H, $CH_2$ at the root of N).

This product is called 4-benzyloxy-3-formylamino-α-[N-benzyl-N-(1-methyl-2-p-hydroxyphenyl)aminomethyl] benzyl alcohol [B].

REFERENCE EXAMPLE 5 a. In 270 ml. of chloroform there was dissolved 27 g. of 4-benzyloxy-3-nitroacetophenone and after adding dropwise to the solution a mixture of 16 g. of bromine and 10 ml. of chloroform gradually, with stirring, the mixture was further stirred for 30 minutes. The reaction mixture was concentrated under reduced pressure and the crystalline residue obtained was washed with a mixture of 50 ml. of benzene and 50 ml. of n-hexane and dried to give 31 g. of 4-benzyloxy-3-nitro-α-bromoacetophenone melting at 135°–136° C.

b. A mixture of 30.5 g. of 4-benzyloxy-3-nitro-α-bromoacetophenone and 28.5 g. of N-benzyl-N-tert-butylamine was refluxed together with 300 ml. of methyl ethyl ketone for 3 hours under heating. After cooling, the precipitates thus formed were filtered off. The filtrate was concentrated under a reduced pressure and the crystals thus formed were recovered and recrystallized from ethanol to give 30 g. of 4-benzyloxy-3-nitro-α-(N-benzyl-N-tert-butylamino)-acetophenone melting at 99°–100° C.

c. In a mixture of 200 ml. of ethanol and 150 ml. of tetrahydrofuran there was dissolved 30 g. of 4-benzyloxy-3-nitro-α-(N-benzyl-N-tert-butylamino)acetophenone and after adding to the solution 3 g. of sodium borohydride, the mixture was stirred for 3 hours at room temperature. The reaction product was concentrated under reduced pressure and after adding water to the residue, the product was extracted with benzene. The extract was washed with water, dried over anhydrous magnesium sulfate, and concentrated under a reduced pressure to give 30 g. of 4-benzyloxy-3-nitro-α-(N-benzyl-N-tert-butylaminomethyl) benzyl alcohol in the form of an oil.

d. In 150 ml. of a 50% aqueous acetic acid solution there was dissolved 30 g. of 4-benzyloxy-3-nitro-α-(N-benzyl-N-tert-butylaminomethyl) benzyl alcohol and after adding to the solution 12 g. of iron powder, the mixture was refluxed for 25 minutes, accompanied by heating. While the reaction mixture was still hot, it was filtered and the filtrate was concentrated under a reduced pressure. Then, after adding to the residue 50 ml. of a 10% aqueous sodium carbonate solution, the product was extracted with benzene. The extract was washed with water, dried over anhydrous magnesium sulfate, and concentrated under reduced pressure to give a crystalline residue. By recrystallizing the product from a mixture of 40 ml. of benzene and 60 ml. of n-hexane, 23 g. of 3-amino-4-benzyloxy-α-(N-benzyl-N-tert-butylaminomethyl) benzyl alcohol melting at 68°–69° C was obtained.

e. In 50 ml. of 5 : 3 acetic anhydride-formic acid there was dissolved 20 g. of 3-amino-4-benzyloxy-α-(N-benzyl-N-tert-butylaminomethyl) benzyl alcohol and after allowing the solution to stand overnight, the solution was concentrated under a reduced pressure. The residue thus obtained was dissolved in 120 ml. of methanol and after adding to the solution 5 ml. of water and 7.5 g. of sodium carbonate, the mixture was stirred for one hour at room temperature. Then, the solvent was distilled off from the reaction mixture under reduced pressure and the residue obtained was extracted with benzene. The extract was washed with water, dried over anhydrous magnesium sulfate, and concentrated under a reduced pressure to give 20.5 g. of 4-benzyloxy-3-formylamino-α-(N-benzyl-N-tert-butylaminomethyl) benzyl alcohol in the form of an oil.

f. In 30 ml. of anhydrous tertrahydrofuran there was dissolved 5 g. of 4-benzyloxy-3-formylamino-α-(N-benzyl-N-tort-butylaminomethyl) benzyl alcohol and the resultant solution was added dropwise, with stirring, to a solution of 20 ml. of tetrahydrofuran and 20 ml. of ether to which there had been added 3 g. of lithium aluminum hydride. Thereafter, the resultant mixture was refluxed for one hour, accompanied by heating. Then, after adding dropwise 20 ml. of water to the reaction mixture gradually followed by stirring for one hour, the reaction mixture was filtered and the filtrate was concentrated under a reduced pressure. The residue was extracted with benzene and the extract was washed with water, dried, and concentrated under reduced pressure. The residue was subjected to a silica gel (70 ml.) column chromatography, the 3rd-8th fractions (each fraction 40 ml.) were collected by using chloroform as an eluting agent and concentrated under reduced pressure to provide 2.8 g. of a faint-yellow oily 4-benzyloxy-3-methylamino-α-(N-benzyl-N-tert-butylaminomethyl) benzyl alcohol.

g. In 5 ml. of 5 : 3 acetic anhydride-formic acid mixture there was dissolved 1.5 g. of 4-benzyloxy-3-methylamino-α-(N-benzyl-N-tert-butylaminomethyl) benzyl alcohol and the solution was allowed to stand overnight. The mixture was then concentrated under reduced pressure, the residue formed was dissolved in 50 ml. of methanol, and after adding to the solution 3 ml. of chilled water and 2 g. of sodium carbonate, the resultant mixture was stirred for one hour. The reaction product was concentrated under reduced pressure and the residue obtained was extracted with benzene. After washing the extract with water followed by drying over magnesium sulfate, the solvent was distilled off under reduced pressure to give 1.5 g. of a brownish oily 4-benzyloxy-3-(N-methyl-N-formylamino)-α-(N-benzyl-N-tert-butylaminomethyl) benzyl alcohol.

REFERENCE EXAMPLE 6 a. In 100 ml. of chloroform there was dissolved 16.5g. of p-nitroacetophenone and after adding dropwise to the solution 16 g. of bromine at room temperature, the mixture was stirred for 30 minutes. When the solvent was distilled off from the mixture under reduced pressure, a yellow crystalline material was obtained. By recrystallizing the crystals from benzene-n-hexane, 18.8 g. of 4-nitro-α-bromoacetophenone melting at 100°–101° C was obtained. The yield was 77%.

| | Elemental analysis for $C_8H_6NO_3Br$: | | | |
|---|---|---|---|---|
| | C(%) | H(%) | N(%) | Br(%) |
| Calculated: | 39.37 | 2.48 | 5.74 | 32.74 |
| Found: | 39.22 | 2.30 | 5.41 | 32.33 | b. In 50 ml. of anhydrous acetonitrile there was dissolved 10 g. of α-bromo-4-nitroacetophenone and after adding to the solution 13.7 g. of N-benzyl-N-tert-butylamine at normal temperature, the mixture was stirred for 2 hours. After distilling off the solvent under reduced pressure from the mixture, 100 ml. of benzene was added to the residue and after filtering off the hydrobromide of N-benzyl-N-tert-butylamine which had formed, benzene was distilled off under reduced pressure to give a red-black liquid. When 10 ml. of ethanol was added to the liquid, a crystalline material was formed, which was recovered by filtering and recrystallizing from ethanol to provide 3.5 g. of yellow acicular crystals of 4-nitro-α-(N-benzyl-N-tert-butylamino)-acetophenone melting at 88°–90° C.

| | Elemental analysis for $C_{19}H_{22}N_2O_3$: | | |
|---|---|---|---|
| | C(%) | H(%) | N(%) |
| Calculated: | 69.92 | 6.79 | 8.58 |
| Found: | 69.73 | 6.81 | 8.71 | c. In 200 ml. of ethanol there was dispersed 5 g. of 4-nitro-α-(N-benzyl-N-tert-butylamino)acetophenone and after adding to the dispersion 1 g. of sodium borohydride, the mixture was stirred at room temperature, whereby the acetophenone dissolved gradually. When the compound dissolved completely, the solution was stirred for 30 minutes and then the solvent was distilled off under reduced pressure to give yellow crystals. By recrystallizing these crystals from ethanol, 4 g. of yellow acicular crystals of 4-nitro-α-(N-benzyl-N-tert-butylaminomethyl) benzyl alcohol melting at 111°–112° C were obtained.

| | Elemental analysis for $C_{19}H_{24}N_2O_3$: | | |
|---|---|---|---|
| | C(%) | H(%) | N(%) |
| Calculated: | 69.49 | 7.37 | 8.53 |

-continued

Elemental analysis for $C_{19}H_{24}N_2O_3$:

|  | C(%) | H(%) | N(%) |
|---|---|---|---|
| Found: | 69.19 | 7.49 | 8.72 | d. In 100 ml. of anhydrous methanol there was dissolved 4 g. of 4-nitro-α-(N-benzyl-N-tert-butylaminomethyl) benzyl alcohol and after adding to the solution 1 g. of Raney nickel, the catalytic reduction was conducted at normal temperature and pressure until 1080 ml. of hydrogen was absorbed. After filtering off the catalyst, the solvent was distilled off under a reduced pressure to provide an oily material. By purifying the oily material by means of a 100 ml. silica gel column and using benzene as a developing solvent, a yellow liquid was obtained. When the liquid was allowed to stand at room temperature, a crystalline material was formed, which was recovered by filtration and recrystallized from ethanol-n-hexane to provide 2.13 g. of yellow acicular crystals of 4-amino-α-(N-benzyl-N-tert-butylaminomethyl) benzyl alcohol melting at 88°–90° C.

Elemental analysis for $C_{19}H_{26}N_2$:

|  | C(%) | H(%) | N(%) |
|---|---|---|---|
| Calculated: | 76.47 | 8.78 | 9.39 |
| Found: | 76.59 | 9.11 | 9.53 | e. In 10.6 ml. of 5 : 3 acetic anhydride-formic acid mixture there was dissolved 2.13 g. of 4-amino-α-(N-benzyl-N-tert-butylaminomethyl) benzyl alcohol and the solution was stirred overnight at room temperature. Then, when the excessive acetic anhydride and formic acid were distilled off under reduced pressure, an oily material was obtained. The product was dissolved in 30 ml. of methanol and after adding to the solution 5 ml. of water and an excessive amount of sodium carbonate, the resultant mixture was stirred for one hour at room temperature. The solvent was then distilled off from the reaction mixture under reduced pressure, the oily material thus obtained was dissolved in 50 ml. of benzene, and the solution was washed with water until the washing became neutral. After drying the solution over anhydrous magnesium sulfate, the solvent was distilled off under reduced pressure to give 2 g. of caramel-like 4-formylamino-α-(N-benzyl-N-tert-butylaminomethyl)-benzyl alcohol.

The nuclear magnetic resonance spectra and infrared absorption spectra of the product coincided with those of the presumed structure.

REFERENCE EXAMPLE 7 a. In 200 ml. of methanol there was dissolved 16.0 g. of 4-benzyloxy-3-formylamino-α-[N-benzyl-N-(1-methyl-2-p-hydroxyphenylethyl) aminomethyl] benzyl alcohol [A] prepared in Reference Example 4 and after adding to the solution 30 ml. of 4.8 normal hydrochloric acid, the mixture was refluxed for one hour and 30 minutes under heating. After the reaction was completed, the reaction product was cooled and after adding thereto 10 g. of potassium hydroxide and 50 ml. of water, the resultant mixture was stirred for one hour. The solvent was distilled off from from the reaction product under reduced pressure and the residue obtained was extracted with benzene. The extract was washed with water, dried over anhydrous magnesium sulfate, and then concentrated under reduced pressure to provide 14.5 g. of a crystalline powder of 3-amino-4-benzyloxy-α-[N-benzyl-N-(1-methyl-2-p-hydroxyphenylethyl) aminomethyl] benzyl alcohol [A].

b. In 20 ml. of acetic anhydride there was dissolved 4.0 g. of 3-amino-4-benzyloxy-α-[N-benzyl-N-(1-methyl-2-p-hydroxyphenylethyl)aminomethyl] benzyl alcohol [A] prepared above and after heating the mixture to 65°–80° C for one hour and 30 minutes, the reaction mixture was concentrated under reduced pressure. The residue was dissolved in a mixture of 15 ml. of methanol and 2.0 g. of potassium hydroxide and the solution was stirred for one hour at room temperature. Then, methanol was distilled off under reduced pressure and after water was added to the residue, the residue was extracted with benzene. The extract was washed with water, dried over anhydrous magnesium sulfate, and dried. Thereafter, by distilling off the solvent, 3.8 g. of a crystalline powder of 4-benzyloxy-3-acetylamino-α-[N-benzyl-N-(1-methyl-2-p-hydroxyphenylethyl)aminomethyl] benzyl alcohol [A] was obtained. By recrystallizing 2.0 g. of the product thus obtained from 20 ml. of ethanol 1.6 g. of the crystalline pure product was obtained, melting at 141°–143° C.

Elemental analysis for $C_{32}H_{36}N_2O_4$:

|  | C(%) | H(%) | N(%) |
|---|---|---|---|
| Calculated: | 75.55 | 6.92 | 5.34 |
| Found: | 75.62 | 7.03 | 5.21 |

REFERENCE EXAMPLE 8.

In 20 ml. of anhydrous pyridine there was dissolved 2 g. of 3-amino-4-benzyloxy-α-[N-benzyl-N-(1-methyl-2-p-hydroxyphenylethyl)-aminomethyl]benzyl alcohol (prepared in the aforesaid Reference Example 7-a) and the solution was cooled to temperatures from −20° to −30° C. A solution of 2.28 g. of benzyloxyacetyl chloride in 5 ml. of toluene was added dropwise to the solution thus cooled and while stirring the mixture, the temperature of the mixture was elevated slowly to room temperature. After stirring the mixture overnight, the solvent was distilled off under reduced pressure and the residue was mixed with 50 ml. of water. After washing the benzene solution thus obtained with water, benzene was distilled off from the reaction mixture under reduced pressure to provide a red oily material. The product was dissolved in 50 ml. of ethanol and after adding to the solution 5 ml. of water and 10 ml. of 4N sodium hydroxide solution, the resultant mixture was stirred for two hours. After adjusting the pH of the reaction mixture to 3 by adding 1N hydrochloric acid, an excessive amount of sodium carbonate was added thereto. Then, ethanol was distilled off under reduced pressure and the residue was extracted with benzene. The extract was washed three times with water, dried over anhydrous sodium sulfate, and concentrated under reduced pressure to provide a yellow oily material. The product was then subjected to a silica gel column chromatography (65 ml.). The product was eluted using 9 : 1 benzene-acetone mixture and the effluent was concentrated under reduced pressure to provide 3-benzyloxyacetylamino-4-benzyloxy-α-[N- benzyl-N-(1-methyl-2-p-hydroxyphenylethyl-)aminomethyl]benzyl alcohol.

Nuclear magnetic resonance spectra (CDCl₃):
δ: 1.00 ppm. (d, 3H, CH—CH₃), 4.08 ppm.

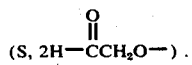

(S, 2H—CCH₂O—).

The invention will further be illustrated by the following examples. These examples are however not to be considered as limiting.

EXAMPLE 1

In 20 ml. of ethanol there was dissolved 1.4 g. of 4-benzyloxy-3-formylamino-α-(N-benzyl-N-isopropylaminomethyl)-benzyl alcohol and after adding to the solution 0.2 g. of 10% palladium carbon, the catalytic reduction was carried out at normal temperature and pressure. After 165 ml. of hydrogen was absorbed, the reaction was stopped. The catalyst was filtered off, the solvent was distilled off under reduced pressure, and then the residue thus formed was dissolved in a small amount of ethanol. Thereafter, when a small amount of ether was added to the solution and the solution was allowed to stand, a crystalline material was formed. By recovering the crystalline material by filtration, 0.7 g. of 3-formylamino-4-hydroxy-α-(isopropylaminomethyl)benzyl alcohol was obtained.

When 120 mg. of the product obtained above was added to 2 ml. of ethanol solution containing 30 mg. of fumaric acid and the mixture then allowed to stand, a white crystalline material was precipitated. The crystals were recovered by filtration to provide 3-formylamino-4-hydroxy-α-(isopropylaminomethyl)benzyl alcohol ½ fumarate melting at 179°–190° C. (decomposed).

| Elemental analysis for C₁₄H₂₀N₂O₅: | | | |
|---|---|---|---|
| | C(%) | H(%) | N(%) |
| Calculated: | 56.75 | 6.80 | 9.45 |
| Found: | 56.71 | 6.76 | 9.70 |

EXAMPLE 2

In 100 ml. of methanol there was dissolved 2.3 g. of 4-benzyloxy-3-benzyloxyacetylamino-α-(N-benzyl-N-isopropylaminomethyl)benzyl alcohol and after adding to the solution 4.3 ml. of 1N hydrogen chloride in ethanol solution and then 0.3 g. of 10% palladium carbon, the catalytic reduction was conducted at normal temperature and pressure. When 300 ml. of hydrogen was absorbed, the reaction was stopped. Thereafter, the catalyst was filtered off and then the solvent was distilled off under reduced pressure to provide a white crystalline material. By crystallizing the crystals from methanol-n-hexane, 600 mg. of 4-hydroxy-3-hydroxyacetylamino-α-(isopropylaminomethyl)benzyl alcohol hydrochloride melting at 188°–190° C was obtained.

| Elemental analysis for C₁₂H₂₀N₂O₄ . HCl: | | | |
|---|---|---|---|
| | C(%) | H(%) | N(%) |
| Calculated: | 51.23 | 6.95 | 9.19 |
| Found: | 50.79 | 7.03 | 9.03 |

EXAMPLE 3

In 30 ml. of ethanol there was dissolved 2.5 g. of 4-benzyloxy-3-formylamino-α-(N-benzyl-N-tert-butyalminomethyl)-benzyl alcohol and after adding to the solution 0.2 g. of 10% palladium carbon, the catalytic reaction was conducted at normal temperature and pressure. When 280 ml. of hydrogen was absorbed, the reaction was stopped. After filtering off the catalyst, the reaction product was concentrated under reduced pressure to give 1.3 g. of a crystalline powder of 3-formylamino-4-hydroxy-α-(tert-butylaminomethyl)benzyl alcohol. When 1.2 g. of the product was adding to 15 ml. of ethanol having dissolved therein 0.3 g. of fumaric acid and the mixture was allowed to stand overnight at —4° C, a white crystalline material was formed. By recovering the crystals at filtration, 1.14 g. of 3-formylamino-4-hydroxy-α-(tert-butylaminomethyl) benzyl alcohol ½ fumarate was obtained melting at 195°–196° C.

| Elemental analysis for C₁₅H₂₂N₂O₅: | | | |
|---|---|---|---|
| | C(%) | H(%) | N(%) |
| Calculated: | 58.05 | 7.15 | 9.03 |
| Found: | 58.03 | 7.21 | 8.94 |

EXAMPLE 4

In 10 ml. of methanol there was dissolved 0.7 g. of 4-benzyloxy-3-formylamino-α-(N-isopropyl-N-benzylamino)acetophenone and after adding to the solution 0.2 g. of 10% palladium carbon, the catalyst reduction was carried out at normal pressure and temperature. When 120 ml. of hydrogen was absorbed, the reaction was stopped. After filtering off the catalyst, the reaction product was concentrated to give 0.3 g. of crude 3-formylamino-4-hydroxy-α-(N-isopropylaminomethyl)benzyl alcohol. When 240 mg. of this product was dissolved in 3 ml. of ethanol and after adding to the solution 60 mg. of fumaric acid, the mixture was allowed to stand at room temperature to form a crystalline material, which was recovered by filtration to provide 75 mg. of 3-formylamino-4-hydroxy-α-(isopropylaminomethyl)benzyl alcohol ½ fumarate melting at 179°–181° C.

The product showed the same infrared absorption spectra as the product obtained in Example 1.

EXAMPLE 5

In 20 ml. of ethanol there was dissolved 1 g. of 4-benzyloxy-3-formylamino-α-(N-benzyl-N-tert-butylamino)acetophenone and after adding to the solution 0.2 g. of 10% palladium carbon, the catalytic reduction was conducted at normal temperature and pressure. When 165 ml. of hydrogen was absorbed, the reaction was stopped. After filtering off the catalyst, the reaction product was concentrated to give 0.5 g. of crude 3-formylamino-4-hydroxy-α-(tert-butylaminomethyl) benzyl alcohol. When 250 mg. of the product was added to 5 ml. of ethanol solution having dissolved therein 60mg. of fumaric acid and then the mixture was allowed to stand at room temperature, a crystalline material was formed, which was recovered by filtration to provide 100mg. of 3-formylamino-4-hydroxy-α-(tert-butylaminomethyl) benzyl alcohol . ½ fumarate melting at 195°–196° C.

The product showed the same infrared absorption spectra as the compound prepared in Example 3.

EXAMPLE 6

In 10 ml. of ethanol there was dissolved 0.45 g. of 3-formylamino-4-hydroxy-α-(N-benzyl-N-isopropylaminomethyl)-benzyl alcohol and after adding to the solution 0.1 g. of 10% palladium carbon, the catalystic reduction was carried out at normal temperature and pressure. When 36 ml. of hydrogen was absorbed, the reaction was stopped. After filtering off the catalyst, the reaction product was concentrated under reduced pressure to give 0.32 g. of a white crystalline powder of 3-formylamino-4-hydroxy-α-(isopropylaminomethyl) benzyl alcohol. When 240 mg. of the product was dissolved in 3 ml. of ethanol and after adding thereto 60 mg. of fumaric acid, the mixture was allowed to stand at room temperature. There was thus obtained 250 mg. of white crystals of 3-formylamino-4-hydroxy-α-(isopropylaminomethyl)-benzyl alcohol . ½ fumarate.

The product showed the same infrared absorption spectra as the product obtained in Example 1.

EXAMPLE 7

In 10 ml. of ethanol there was dissolved 0.9 g. of 3-formylamino-4-hydroxy-α-(N-benzyl-N-tert-butylaminomethyl) benzyl alcohol and after adding to the solution 0.1 g. of 10% palladium carbon, the catalytic reduction was carried out at normal temperature and pressure. When 65 ml. of hydrogen was absorbed, the reaction was stopped. After filtering off the catalyst, the reaction product was concentrated under a reduced pressure to give 0.65 g. of a white crystalline powder of 3-formylamino-4-hydroxy-α-(tert-butylaminomethyl)benzyl alcohol. When 500 mg. of the product was dissolved in 5 ml. of ethanol and after adding to the solution 120 mg. of fumaric acid, the mixture was allowed to stand at room temperature. There was thus formed a crystalline product. The crystals were recovered by filtration to provide 520 mg. of 3-formylamino-4-hydroxy-α-(tert-butylaminomethyl)-benzyl alcohol . ½ fumarate.

The product showed the same infrared absorption spectra as the product prepared in Example 3.

EXAMPLE 8

In 20 ml. of ethanol there was suspended 1.1 g. of the 4-benzyloxy-3-formylamino-α-[N-benzyl-N-(1-methyl-2-p-hydroxyphenylethyl)aminomethyl]benzyl alcohol [A] prepared by the procedure in Reference Example 4 and after adding to the suspension 0.1 g. of 10% palladium carbon, the catalytic reduction was conducted at normal temperature and pressure until 105 ml. of hydrogen was absorbed. After filtering off the catalyst, the reaction product was concentrated under reduced pressure to give 0.7 g. of a white crystalline powder of 3-formylamino-4-hydroxy-α-[N-(1-methyl-2-p-hydroxyphenylethyl)aminomethyl]-benzyl alcohol [A].

When 0.34 g. of the product prepared above was dissolved in 95% ethanol together with 0.06 g. of fumaric acid and the solution was allowed to stand, crystals were formed which were recovered to provide 0.33 g. of 3-formylamino-4-hydroxy-α-[N-(1-methyl-2-p-hydroxyphenylethyl)aminomethyl]benzyl alcohol [A] . ½ fumarate melting at 151°–153° C.

| Elemental analysis for $C_{20}H_{24}N_2O_5$: | | |
|---|---|---|
| | C(%) | H(%) | N(%) |
| Calculated: | 61.85 | 6.23 | 7.21 |
| Found: | 61.52 | 6.31 | 7.31 |

EXAMPLE 9

In 10 ml. of ethanol there was dissolved 1.0 g. of 4-benzyloxy-3-formylamino-α-[N-benzyl-N-(1-methyl-2-p-hydroxyphenylethyl)-aminomethyl]benzyl alcohol [B] prepared by the procedure in Reference Example 4 and after adding to the solution 0.1 g. of 10% palladium carbon, the catalytic reduction was conducted at normal temperature and pressure until 95 ml. of hydrogen was absorbed. After filtering off the catalyst, the reaction product was concentrated under reduced pressure to give 0.65 g. of a faint-brownish powder of 3-formylamino-4-hydroxy-α-[N-(1-methyl-2-p-hydroxyphenylethyl)aminomethyl]benzyl alcohol [B].

When 0.34 g. of the product prepared above was dissolved in 95% ethanol together with 0.06 g. of fumaric acid and the solution was allowed to stand, crystals were formed which were recovered to provide 0.3 g of 3-formylamino-4-hydroxy-α-[N-(1-methyl-2-p-hydroxyphenylethyl)aminomethyl]benzyl alcohol [B] ½ fumarate melting at 154.1°–155° C.

| Elemental analysis for $C_{20}H_{24}N_2O_5$: | | |
|---|---|---|
| | C(%) | H(%) | N(%) |
| Calculated: | 61.85 | 6.23 | 7.21 |
| Found: | 61.73 | 6.27 | 7.19 |

EXAMPLE 10

In 20 ml. of ethanol there was dissolved 1.5 g. of 4-benzyloxy-3-formylamino-α-[N-benzyl-N-(1-methyl-3-cyclohexylpropyl)aminomethyl]benzyl alcohol and after adding to the solution 0.2 g. of 10% palladium carbon, the catalytic reduction was conducted at normal temperature and pressure until 140 ml. of hydrogen was absorbed. After filtering off the catalyst, the reaction product was concentrated under a reduced pressure to provide 0.9 g. of a white crystalline powder of 3-formylamino-4-hydroxy-α-[N-(1-methyl-3-cyclohexylpropyl)aminomethyl]benzyl alcohol.

When 470 mg. of the product was dissolved in 7 ml. of 0.2N acetic acid in ethanol solution, the solution was concentrated up to 2-3 ml., and after adding thereto ether, the mixture was allowed to stand. White crystals were formed. The crystals were recovered by filtration to provide 0.5 g. of 3-formylamino-4-hydroxy-α-[N-(1-methyl-3-cyclohexylpropyl)aminomethyl]benzyl alcohol acetate melting at 138°–140° C.

| Elemental analysis for $C_{21}H_{34}N_2O_5$: | | |
|---|---|---|
| | C(%) | H(%) | N(%) |
| Calculated: | 63.94 | 8.69 | 7.10 |
| Found: | 64.31 | 8.92 | 7.46 |

EXAMPLE 11

In 30 ml. of ethanol there was dissolved 2.7 g. of 4-benzyloxy-3-methylamino-α-(N-benzyl-N-tert-butylaminomethyl)benzyl alcohol prepared by the procedure described in Reference Example 5-f and after adding to the solution 0.3 g. of 10% palladium carbon, the catalytic reduction was carried out at normal temperature and pressure until 310 ml. of hydrogen was absorbed. After filtering off the catalyst, the reaction product was concentrated under a reduced pressure to provide 1.3 g. of 4-hydroxy-3-methylamino-α-(tert-butylaminomethyl)benzyl alcohol in the form of a powder. When ethanol was added to the product, a white crystalline material was formed. The product, when recrystallized from ethanol, melted at 173° C.

| | Elemental analysis for $C_{13}H_{22}N_2O_2$: | | |
|---|---|---|---|
| | C(%) | H(%) | N(%) |
| Calculated: | 65.52 | 9.30 | 11.75 |
| Found: | 65.43 | 9.57 | 11.52 |

EXAMPLE 12

In 20 ml. of ethanol there was dissolved 1.4 g. of 4-benzyloxy-3-(N-methyl-N-formylamino)-α-(N-benzyl-N-tert-butylaminomethyl)-benzyl alcohol prepared in Reference Example 5-g and after adding to the solution 0.1 g. of 10% palladium carbon, the catalytic reduction was conducted until 150 ml. of hydrogen was absorbed. After filtering off the catalyst, the reaction product was concentrated under reduced pressure to provide 0.8 g. of a white crystalline powder of 4-hydroxy-3-(N-methyl-N-formylamino)-α-tert-butylaminomethylbenzyl alcohol. When 360 mg. of the product was dissolved in 6 ml. of ethanol together with 85 mgs. of fumaric acid and the solution was allowed to stand, a white crystalline material was formed. The crystals were recovered by filtration to provide 390 mgs. of 4-hydroxy-3-(N-methyl-N-formylamino)-α-tert-butylaminomethylbenzyl alcohol . ½ fumarate melting at 188° C.

| | Elemental analysis for $C_{15}H_{24}N_2O_5$: | | |
|---|---|---|---|
| | C(%) | H(%) | N(%) |
| Calculated: | 59.24 | 7.46 | 8.64 |
| Found: | 59.16 | 7.47 | 8.34 |

EXAMPLE 13

In 100 ml. of anhydrous methanol there was dissolved 1.8 g. of 4-formylamino-α-(N-benzyl-N-tert-butylaminomethyl)benzyl alcohol and after adding to the solution 100 mg. of 10% palladium carbon, the catalytic reduction was conducted at normal temperature and pressure until the absorption of hydrogen stopped completely. After filtering off the catalyst, the solvent was distilled off under reduced pressure from the reaction product to provide 1.46 g. of a caramel-like material. The product was dissolved in 20 ml. of ethanol and after adding to the solution 358 mg. of fumaric acid, the mixture was allowed to stand at 4° C, whereby a white acicular crystalline material was precipitated, which was recovered by filtration to give 950 mg. of 4-formylamino-α-(N-tert-butylaminomethyl)-benzyl alcohol . ½ fumarate melting at 125°–127° C.

| | Elemental analysis for $C_{15}H_{22}N_2O_4$: | | |
|---|---|---|---|
| | C(%) | H(%) | N(%) |
| Calculated: | 61.21 | 7.53 | 9.52 |
| Found: | 60.93 | 7.70 | 9.23 |

EXAMPLE 14

In 15 ml. of ethanol there was dissolved 1.1 g. of 3-formylamino-α-(N-benzyl-N-tert-butylaminomethyl)benzyl alcohol and after adding to the solution 0.1 g. of 10% palladium carbon, the catalytic reduction was conducted at normal temperature and pressure until 76 ml. of hydrogen was absorbed. After filtering off the catalyst, the reaction product was concentrated under reduced pressure to give 750 mg. of a white crystalline powder.

Thereafter, 470 mg. of the product prepared above and 116 mg. of fumaric acid were dissolved in 3 ml. of ethanol and after adding ether to the solution until the solution became slightly turbid, the mixture was allowed to stand, whereby a white crystalline material was formed, which was recovered by filtration to provide 530 mg. of 3-formylamino-α-(N-tert-butylaminomethyl)benzyl alcohol . ½ fumarate melting at 182° C.

| | Elemental analysis for $C_{15}H_{22}N_2O_4$: | | |
|---|---|---|---|
| | C(%) | H(%) | N(%) |
| Calculated: | 61.21 | 7.53 | 9.52 |
| Found: | 61.16 | 7.76 | 9.44 |

Reference Example 9

In 30 ml. of anhydrous pyridine there were dissolved 4g. of 3-amino-4-benzyloxy-α-[N-benzyl-N-(1-methyl-2-p-hydroxyphenylethyl)-aminomethyl]benzyl alcohol hydrochloride and 3.5 g of N-acetyl-β-alanine and after adding to the solution 5.5 g. of dicyclohexylcarbodiimide under ice-cooling, the mixture was stirred overnight. After filtering off the precipitates thus formed, the reaction mixture was concentrated under reduced pressure and the residue was dissolved in 30 ml. of methanol. Then, after adding to the solution 10 ml. of 4N sodium hydroxide solution, the mixture was stirred for 3 hours and further after adding thereto 1N hydrochloric acid solution to adjust the pH to 3 and adding excessive sodium carbonate, the resultant mixture was stirred for 30 minutes. The reaction product was concentrated under a reduced pressure and then extracted with 50 ml. of chloroform. The extract was washed three times with water, dried over anhydrous magnesium sulfate, and concentrated under reduced pressure to five 4 g. of a yellow oily material. By subjecting the product to a silica gel column chromatography (75 ml.) and further to a silica gel column chromatography (35 ml.), 800 mg. of a pure caramel-like 3-(N-acetyl-β-alanyl)amino-4-benzyloxy-α-[N-benzyl-N-(1-methyl-2-p-hydroxyphenylethyl)aminomethyl]benzyl alcohol was obtained. In the above chromatographic purification treatments, 4 : 2 : 1 ethyl acetate-benzene-methanol was used as the developing solvent.

| Elemental analysis for $C_{26}H_{30}N_2O_5$: | | |
| --- | --- | --- |
| | C(%) | H(%) | N(%) |
| Calculated: | 72.58 | 6.94 | 7.05 |
| Found: | 72.44 | 6.98 | 6.86 |

Reference Example 10 a. A mixture of 4.1 g. of 4-benzyloxy-3-nitro-α-bromoacetophenone, 6.6 g. of N-benzyl-N-(1-methyl-2-p-acetylaminophenyl)ethyl)amine, and 41 ml. of methyl ethyl ketone was heated to 65°–80° C for one hour. After cooling the reaction mixture, the precipitates thus formed were filtered off and the filtrate was concentrated under reduced pressure. The residue thus formed was dissolved in 40 ml. of ethanol at temperatures below 50° C and the solution was allowed to stand at room temperature to form crystals which were recovered by filtration to give 3.7 g. of 4-benzyloxy-3-nitro-α-[N-benzyl-N-(1-methyl-2-p-acetylaminophenylethyl)amino]acetophenone.

b. In 30 ml. of methanol there was suspended 2.7 g. of 4-benzyloxy-3-nitro-α-[N-benzyl-N-(1-methyl-2-p-acetylaminophenylethyl)amino]acetophenone and after adding to the suspension 0.6 g. of sodium borohydride under ice-cooling, the mixture was stirred for one hour. After adding water to the reaction mixture and distilling off methanol thereform under a reduced pressure, the product was extracted with benzene. The extract was washed with water, dried over anhydrous magnesium sulfate, and concentrated under reduced pressure to give 2.6 g. of a yellowish powder of 4-benzyloxy-3-nitro-α-[N-benzyl-N-(1-methyl-2-p-acetylaminophenylethyl)aminomethyl]benzyl alcohol.

c. In 20 ml. of methanol there was dissolved 1.3 g. of 4-benzyloxy-3-nitro-α-[N-benzyl-N-(1-methyl-2-p-acetylaminophenylethyl)aminomethyl]benzyl alcohol and after adding to the solution 0.7 g. of iron powder, 0.6 ml. of 4.8 N hydrochloric acid and 3 ml. of water and the mixture was refluxed for 2 hours and 30 minutes. After filtering off insoluble materials from the reaction mixture, 0.8 g. of sodium carbonate was added and stirred for 2 hours. To the reaction mixture thus obtained there was added water; methanol was distilled off under reduced pressure and extracted with benzene. The extract was washed with water, dried over anhydrous magnesium sulfate, and concentrated under reduced pressure to give 1.1 g. of a crystalline powder of 3-amino-4-benzyloxy-α-[N-benzyl-N-(1-methyl-2-p-acetylaminophenylethyl)-aminomethyl]benzyl alcohol.

d. In 6 ml. of 5 : 3 acetic anhydride-formic acid there was dissolved 1.0 g. of 3-amino-4-benzyloxy-α-[N-benzyl-N-(1-methyl-2-p-acetylaminophenylethyl-)aminomethyl]benzyl alcohol and after allowing to stand overnight, the reaction mixture was concentrated under reduced pressure. The residue was dissolved in a mixture of 10 ml. of methanol and 2 ml. of water and after adding to the solution 0.5 g. of potassium hydroxide, the mixture was stirred for one hour at room temperature. Then, methanol was distilled off from the reaction mixture under reduced pressure; the residue was mixed with water and extracted with benzene. Thereafter, the extract was washed with water, dried over anhydrous magnesium sulfate, and the solvent was distilled off therefrom to provide 0.9 g. of a crystalline powder of 4-benzyloxy-3-formylamino-α-[N-benzyl-N-(1-methyl-2-p-acetylaminophenylethyl)aminomethyl]-benzyl alcohol.

Nuclear magnetic resonance spectra (CDCl$_3$)

δ: 2.04 ppm (S, 3H, H of the methyl group of p-acetylamino), 8.38 ppm (S, 1H, H of the formyl group), 4.4 ppm (m, 1H, H of the methine group at the root of hydroxyl group).

In the following reference examples the same procedure as above was repeated using different starting materials.

A. By using 2.7 g. of 4-benzyloxy-3-nitro-α-bromoacetophenone and 4.8 g. of N-benzyl-N-(1-methyl-2-{3,4,5-trimethoxyphenyl}-ethyl)amine as the starting materials, 1.2 g. of a crystalline powder of 4-benzyloxy-3-formylamino-α-[N-benzyl-N-(1-methyl-2-{3,4,5-trimethoxyphenyl}ethyl)aminomethyl]benzyl alcohol was obtained.

Nuclear magnetic resonance spectra (CDCl$_3$)

δ: 3.6 ppm., 3.7 ppm. (9H, H of the methyl group of 3,4,5-trimethoxy group), 8.36 ppm. (S, 1H, H of formyl group), 4.46 ppm. (m, 1H, H of the methine group at the root of hydroxyl group).

B. By using 10.4 g. of 4-benzyloxy-3-nitro-α-bromoacetophenone and 15.2 g. of N-benzyl-N-(1-methyl-3-p-hydroxyphenylpropyl)-amine as the starting materials, 5.9 g. of 4-benzyloxy-3-formylamino-α-[N-benzyl-N-(1-methyl-3-p-hydroxyphenylpropyl-)aminomethyl]benzyl alcohol was obtained.

Nuclear magnetic resonance spectra (CDCl$_3$):

δ: 1.76 ppm. (m, 2H, H of the methylene group at the 2-position of 3-p-hydroxyphenylpropyl group), 8.38 (S, 1H, H of formyl group), 4.56 ppm. (m, 1H, H of the methine group at the root of hydroxyl group).

C. By using 6.75 g. of 4-benzyloxy-3-nitro-α-bromoacetophenone and 9.2 g. of N-benzyl-N-p-tolylisopropylamine as the starting materials, 3.7 g. of 3-formylamino-4-benzyloxy-α-[N-benzyl-N-(1-methyl-2-p-tolylethyl)aminomethyl]benzyl alcohol was obtained.

Nuclear magnetic resonance spectra (CDCl$_3$):

δ: 2.30 ppm. (S, 3H, φ—CH$_3$), 5.02 ppm. (S, 2H, —OCH$_2$—).

d. By using 7.55 g. of 4-benzyloxy-3-nitro-α-bromoacetophenone and 11.6 g. of N-benzyl-N-(1-ethyl-2-p-methoxyphenyletyl) amine as the starting materials, 1.5 g. of 3-formylamino-4-benzyloxy-α-[N-benzyl-N-(1-ethyl-2-p-methoxyphenylethyl-)aminomethyl] benzyl alcohol was obtained.

| Elemental analysis for $C_{26}H_{30}N_2O_4$: | | |
| --- | --- | --- |
| | C(%) | H(%) | N(%) |
| Calculated: | 75.81 | 7.11 | 5.20 |
| Found: | 75.67 | 7.25 | 5.37 |

Reference Example 11 a. A mixture of 9.4 g. of 4-benzyloxy-3-nitro-α-bromoacetophenone and 13.7 g. of N-benzyl-N-(1-methyl-2-p-methoxyphenylethyl)amine was heated together with 50 ml. of methyl ethyl ketone to 70°–80° C. for one hour. After cooling the solution and filtering off the precipitates thus formed, the filtrate was concentraed under reduced pressure and ethanol was added to the residue whereby crystals were formed. The crystals were recovered by filtration and recrystallized from ethanol to give 12.8 g. of 4-benzyloxy-3-nitro-α-[N- benzyl-N-(1-methyl-2-p-methoxyphenylethyl-)amino]acetophenone melting at 100°–102° C.

b. In 200 1ml. of ethanol there was suspended 12.8 g. of 4-benzyloxy-3-nitro-α-[N-benzyl-N-(1-methyl-2-p-methoxyphenylethyl)amino]acetophenone and after adding to the suspension 1.8 g. of sodium borohydride, the mixture was stirred overnight. Then, ethanol was distilled off from the reaction product and after adding water to the residue, the product was extracted with benzene. The extract was washed with water, dried over anhydrous magnesium sulfate, and concentraed under reduced pressure to provide 10.7 g. of yellow oily 4-benzyloxy-3-nitro-α-[N-benzyl-N-(1-methyl-2-p-methoxyphenylethyl)aminomethyl]benzyl alcohol.

c. In 70 ml. of methanol there was dissolved 10.7 g. of 4-benzyloxy-3-nitro-α-[N-benzyl-N-(1-methyl-2-p-methoxyphenylethyl) aminomethyl]benzyl alcohol and after adding to the solution 15 ml. of 2.2 normal hydrochloric acid solution, 10 ml. of water, and 5.4 g. of iron powder, the mixture was refluxed for one hour under heating. After filtering off insoluble materials from the reaction mixture, the filtrate was concentraed under reduced pressure, mixed with 50 ml. of benzene, 10 ml. of water, and 10 g. of sodium carbonae and then extracted with benzene. The extract was washed with water, dried over anhydrous magnesium sulfate, and concentrated under reduced pressure to give 8.8 g. of a yellow carmel-like 3-amino-4-benzyloxy-α-[N-benzyl-N-(1-methyl-2-methoxyphenylethyl)aminomethyl]-benzyl alcohol.

d. In 20 ml. of 5 : 3 acetic anhydride-formic acid there was dissolved 5.5 g. of 3-amino-4-benzyloxy-α-[N-benzyl-N-(1-methyl-2-p-methoxyphenylethyl-)aminomethyl]benzyl alcohol and after allowing the solution to stand overnight at room temperature, the solution was concentrated under reduced pressure. The residue was mixed with 50 ml. of methanol, 3 ml. of water, and 3.5 g. of sodium carbonate and the mixture was stirred for 2 hours at room temperature. Then, methanol was distilled off from the reaction product under reduced pressure and the residue formed was extracted with benzene. The extract was washed with water, dried over anhydrous magnesium sulfate, and then the solvent was distilled off to provide 5.1 g. of a crystalline powder of 4-benzyloxy-3-formylamino-α-[N-benzyl-N-(1-methyl-2-p-methoxyphenylethyl-)aminomethyl] benzyl alcohol. Then, 4.9 g. of the product was dissolved in 20 ml. of methanol and after adding to the solution 1 g fumaric acid, the mixture was concentrated under reduced pressure. When the residue was dissolved in 80 ml. of ethyl acetate and the solution was allowed to stand overnight, crystals were formed. The crystals were recovered by filtration and recrystallized from isopropanol to provide 3.2 g. of white crystals of 4-benzyloxy-3-formylamino-α-[N-benzyl-N-(1-methyl-2-p-methoxyphenylethyl-)aminomethyl]benzyl alcohol . 1-fumarate melting at 173° C.

In 30 ml. of 90% methanol there was suspended 3 g. of the product prepared above and after adding to the suspension 1.5 g. of sodium carbonate followed by stirring for 30 minutes, the mixture was concentrated under reduced pressure. The residue was mixed with 10 ml. of water and extracted with 30 ml. of benzene. The extract was washed with water, dried over anhydrous magnesium sulfate, and then concentrated under a reduced pressure to give 2.3 g. of a white powder.

Nuclear magnetic resonance spectra (CDCl$_3$):

δ: 4.52 ppm. (m, 1H, CH at the root of hydroxyl group), 3.48 ppm. 3.87 ppm. (AB type quartet, 2H, CH$_2$ at the root of N).

This product is 4-benzyloxy-3-formylamino-α-[N-benzyl-N-(1-methyl-2-p-methoxyphenyl)aminomethyl]benzyl alcohol [A].

Furthermore, the solvent was distilled off from the mother liquor left after recovering the crystals of 4-benzyloxy-3-formylamino-α-[N-benzyl-N-(1-methyl-2-p-methoxyphenylethyl)aminomethyl]benzyl alcohol . 1-fumarate [A] in the aforesaid step and the residue was dissolved in 30 ml. of methanol. After adding to the solution 3 ml. of water and 1.5 g. of sodium carbonate followed by stirring for 30 minutes, the mixture was concentrated under reduced pressure. The residue was mixed with 10 ml. of water and extracted with benzene. The extract was washed with water, dried over anhydrous magnesium sulfate, and then the solvent was distilled off to provide 2.3 g. of a faint-brownish powder of 4-benzyloxy-3-formylamino-α-[N-benzyl-N-(1-methyl-2-p-methoxyphenylethyl)-aminomethyl]benzyl alcohol. The product was subjected to the silica gel column chromatography and the effluent obtained using 10 : 1 benzene-ethyl acetate was concentrated under a reduced pressure to give a white powder.

Nuclear magnetic resonance spectra (CDCl$_3$):

δ: 4.40 ppm. (m, 1H, CH at the root of hydroxyl group), 3.73 ppm. (S, 2H, CH$_2$ at the root of N).

This product is 4-benzyloxy-3-formylamino-α-[N-benzyl-N-(1-methyl-2-p-methoxyphenyl)aminomethyl]benzyl alcohol [B].

REFERENCE EXAMPLE 12.

a. A mixture of 7 g. of 4-benzyloxy-3-nitro-α-bromoacetophenone, 12g. of N-benzyl-3-(3, 4-dimethoxyphenyl)-1-methylpropylamine and 50 ml. of ethyl methyl ketone was heated at temperatures of 60°–70° C for one hour. The reaction mixture was concentrated under reduced pressure, and the residue thus obtained was subjected to a silica gel column chromatography (diameter 3 cm, height 7 cm). The product was eluted using benzene and the effluent was concentrated to provide 6 g of 4-benzyloxy-3-nitro-α-[N-benzyl-N-{3-(3,4-dimethoxyphenyl)-1-methylpropyl}amino]acetophenone.

b. To a mixture of 40 ml. of ethanol and 15 ml. of tetrahydrofuran there was added 6 g. of 4-benzyloxy-3-nitro-α-[N-benzyl-N-{3-(3,4-dimethoxyphenyl)-1-methylpropyl}-amino]acetophenone and after adding to the mixture 0.8 g. of sodium bromohydride under ice-cooling, the mixture was stirred for 2 hours. After adding to the reaction mixture 5 ml. of water, the mixture was concentrated under a reduced pressure. The residue was extracted with benzene and the extract was washed with water, dried over anhydrous magnesium sulfate and concentrated to provide 5.6 g. of oily 4-benzyloxy-3-nitro-α-[N-benzyl-N-{3-(3,4-dimethoxyphenyl)-1-methylpropyl}aminomethyl]benzyl alcohol.

c. In 50 ml. of methanol there was dissolved 5 g. of 4-benzyloxy-3-nitro-α-[N-benzyl-N-{3-(3,4-dimethoxyphenyl)-1-methylpropyl}aminomethyl]benzyl alcohol and after adding to the solution 2.5 g. of iron powder and 5 ml. of 2$\underline{N}$ hydrochloric acid, the mixture was refluxed for 50 minutes. After cooling the reaction mixture, the insoluble materials were filtered off, and 5 ml. of a 2$\underline{N}$ potassium hydride methanol solution and 20 ml. of ethyl acetate were added to the filtrate. The insoluble materials were filtered off and the filtrate was concentrated under a reduced pressure. The residue was extracted with benzene, and the extract was washed with water, dried over anhydrous magnesium sulfate and concentrated under a reduced pressure to provide a yellowish brown viscous product. The product thus obtained was dissolved in benzene and after adding n-hexane until the solution became slightly muddy, the solution was allowed to stand whereby 2.7 g. of yellowish brown crystals of 3-amino-4-benzyloxy-α-[N-benzyl-N-{3-(3,4-dimethoxyphenyl)-1-methylpropyl}aminomethyl]benzyl alcohol [A]were obtained. The product was recrystallized from a mixture of benzene and n-hexane and was characterized by a melting point of 115° C.

d. In 6 ml. of chloroform there was dissolved 2.4 g. of 3-amino-4-benzyloxy-α-[N-benzyl-N-{3-(3, 4-dimethoxyphenyl-1-methylpropyl}aminomethyl]benzyl alcohol [A] and after adding to the solution 5 ml. of 5:3 anhydrous acetic acid-formic acid, the mixture was allowed to stand overnight at room temperature. The residue obtained by concentrating the reaction mixture under a reduced pressure was dissolved in 20 ml. of methanol and after adding to the solution 2 ml. of water and 3 g. of sodium bicarbonate, the mixture was stirred for 2 hours. The residue obtained by concentrating the reaction mixture under a reduced pressure was extracted with benzene, and the extract was washed with water, dried over anhydrous magnesium sulfate. By distilling off the solvent from the extract, 2.2 g. of a yellowish, viscous 4-benzyloxy-3-formamideα-{N-benzyl-3-(3, 4-dimethoxyphenyl)-1-methylpropylaminomethyl}-benzyl alcohol [A] was obtained.

Nuclear magnetic resonance spectra (CDCl₃)
δ: 1.00 ppm (3H, d,>CH—CH₃), 3.82 ppm (6H, s, 2-0-CH₃) 4.57 ppm (1H, m,>CH—OH), 5.04 ppm (2H, s,

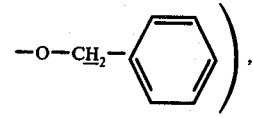

8.34 ppm (1H, s,>N—CHO)

The following products were obtained following the same procedure as described above.

a. By using 3.5 g. of 4-benzyloxy-3-nitro-α-bromoacetophenone and 4.8 g. of N-benzyl-α,α-dimethylphenethylamine as the starting materials, 2.1 g. of white crystals of 4-benzyloxy-3-formamide-α- N-benzyl-N-(α,α-dimethylphenethyl)aminomethyl}benzyl alcohol were obtained melting at 157°–158° C.

| Elemental analysis for C₃₂H₃₆N₂O₃: | | | |
|---|---|---|---|
| | C(%) | H(%) | N(%) |
| Calculated: | 77.92 | 7.13 | 5.51 |
| Found: | 78.03 | 7.24 | 5.42 | b. By using 7 g. of 4-benzyloxy-3-nitro-α-bromoacetophenone and 11.2 g. of N-benzyl-1-methyl-3-p-tolylpropylamine as the starting materials, 2.5 g. of 4-benzyloxy-3-formamide-α-(N-benzyl-1-methyl-3-p-tolylpropylaminomethyl)benzyl alcohol [A] was obtained.

Nuclear magnetic resonance spectra (CDCl₃)
0.97 ppm (3H, d,>CH—CH₃), 2.28 ppm (3H, s, -CH₃) 3.46, 3.86 ppm (2H, AB—q,

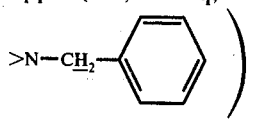

4.54 ppm (1H, m>CH—OH), 5.04 ppm (2H, s,

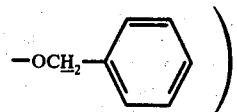

8.33 ppm (1H, s>N—CHO)

c. By using 7 g. of 4-benzyloxy-3-nitro-α-bromoacetophenone and 9 g. of N-benzyl-α-methylphenethylamine as the starting materials, 2.3 g. of a red oily 4-benzyloxy-3-formamide-α-(N-benzyl-α-methylphenethylaminomethyl)benzyl alcohol [A] was obtained. The fumaric acid salt thereof is a white crystalline material melting at 165°–166° C.

| Elemental analysis for C₃₄H₃₄N₂O₇: | | | |
|---|---|---|---|
| | C(%) | H(%) | N(%) |
| Calculated: | 70.80 | 6.27 | 4.59 |
| Found: | 70.59 | 6.19 | 4.87 | d. By using 5.7 g. of 4-benzyloxy-3-nitro-α-bromoacetophenone and 8.2 g. of N-benzyl-3-p-methoxyphenyl-1-methylpropylamine as the starting materials, 1.09 g. of an oily 4-benzyloxy-3-formamide-α-(N-benzyl-3-p-methoxyphenyl-1-methylpropylaminomethyl)-benzyl alcohol [A] was obtained.

Nuclear magnetic resonance spectra (CDCl₃)
δ: 0.98 ppm (3H, d,

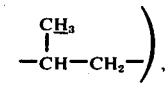

3.75 ppm (3H, s,

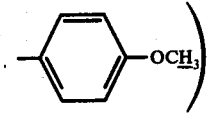

5.02 ppm (2H, s,

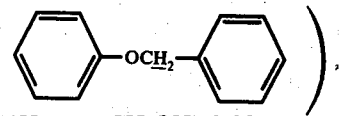

4.50 ppm (1H, m, >CH-OH) 8.32 ppm (1H, s,>N—CHO)

e. By using 8.92 g. of 4-benzyloxy-3-nitro-α-bromoacetophenone and 14.45 g. of N-benzyl-α-methyl-3,4-dimethoxyphenethylamine as the starting materials, 2.15 g. of 4-benzyloxy-3-formamide-α-(N-benzyl-α-methyl-3,4-dimethoxyphenethyl aminomethyl) benzyl alcohol was obtained.

Nuclear magnetic resonance spectra (CDCl₃)
δ: 1.00 ppm (3H, d,>CH-CH₃), 3.81 ppm (6H, s,

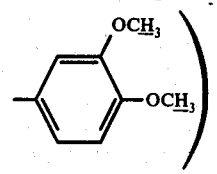

5.04 ppm (2H, s,

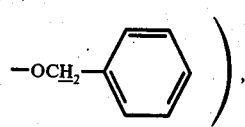

8.36 ppm (1H, s —CHO)

f. By using 3.5 g. of 4-benzyloxy-3-nitro-α-bromoacetophenone and 5.1 g. of N-benzyl-3-(4-hydroxyphenyl)-1-methylpropylamine as the starting materials, 1.5 g. of white crystals of 4-benzyloxy-3-formamide-α-(N-benzyl-3-p-hydroxyphenyl-1-methylpropylaminomethyl)benzyl alcohol [A] was obtained. The product, when recrystallized from isopropanol, melted at 148°–149° C.

Nuclear magnetic resonance spectra (CDCl$_3$)

δ: 0.97 ppm (3H, d,>CH—C$\underline{H}$$_3$), 3.45, 3.81 ppm (2H, AB—q,

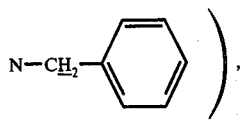

4.48 ppm (1H, m,>C$\underline{H}$—OH), 5.06 ppm (2H, s,

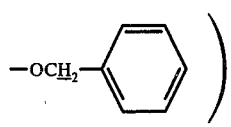

REFERENCE EXAMPLE 13 a. A mixture of 7 g. of 4-benzyloxy-3-nitro-α-bromoacetophenone, 9.6 g. of N-benzyl-1-methyl-2-p-tolylethylamine and 60 ml. of ethyl methyl ketone was refluxed for one hour. After cooling the reaction mixture, the precipitates thus formed were filtered off and the extract was concentrated under a reduced pressure to provide a crystalline residue. The crystalline residue was recrystallized from ethanol to provide 6.5 g. of 4-benzyloxy-3-nitro-α-(N-benzyl-1-methyl-2-p-tolylethylamino)acetophenone melting at 93°–95° C.

b. In a mixture of 50 ml. of ethanol and 30 ml. of tetrahydrofuran there was added 6.5 g. of 4-benzyloxy-3-nitro-α-(N-benzyl-1-methyl-2-p-tolylethylamino)acetophenone and after adding to the mixture 0.7 g. of sodium bromohydride, the mixture was stirred for 3 hours at room temperature. After adding to the reaction mixture 5 ml. of water, the mixture was concentrated under a reduced pressure and the residue thus obtained was extracted with benzene. The extract was washed with water, dried over anhydrous magnesium sulfate and concentrated under a reduced pressure to provide 6.3 g. of viscous 4-benzyloxy-3-nitro-α-(N-benzyl-1-methyl-2-p-tolylethylaminomethyl)benzyl alcohol.

c. In 50 ml. of methanol there was dissolved 6.0 g. of 4-benzyloxy-3-nitro-α-(N-benzyl-1-methyl-2-p-tolylethylaminomethyl)-benzyl alcohol and after adding to the solution 3.0 g. of iron powder and 8 ml. of 2$\underline{N}$ hydrochloric acid, the mixture was refluxed for one hour with stirring. The insoluble materials were filtered off and after adding to the filtrate 4 ml. of 4$\underline{N}$ potassium hydroxide, the insoluble materials thus formed were filtered off, and the extract was concentrated under a reduced pressure. The residue thus obtained was extracted with benzene, and the extract was washed with water, dried over anhydrous magnesium sulfate and concentrated under a reduced pressure. When benzene and n-hexane were added to the residue and the mixture was allowed to stand, yellow crystals were formed. The crystals were recovered by filtration and recrystallized from 3:1 n-hexane-benzene to provide 2.5 g. of crystalline material melting at 117° C.

Nuclear magnetic resonance spectra (CDCl$_3$)

δ: 4.43 ppm (1H, t,>C$\underline{H}$—OH), 3.46, 3.86 ppm (2H, AB—q,

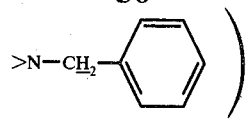

The product thus obtained was 3-amino-4-benzyloxy-α-(N-benzyl-1-methyl-2-p-tolylethylaminomethyl)benzyl alcohol [A].

The solution obtained by removing the above crystals from the mixture of n-hexane and benzene was concentrated, and the residue thus obtained was subjected to a silica gel column chromatography (diameter 3 cm, height 7 cm). The products were eluted using 10:1 benzene-ethylacetate, and the eluates were combined and concentrated to provide 1.5 g. of a faint yellowish viscous product.

Nuclear magentic resonance spectra (CDCl$_3$)

δ: 4.34 ppm (1H, m,>C$\underline{H}$—OH), 3.78 ppm (2H, d,

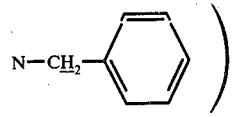

The product thus obtained was 3-amino-4-benzyloxy-α-(N-benzyl-1-methyl-2-p-tolylethylaminomethyl)benzyl alcohol [B].

d. In 8 ml. of chloroform there was dissolved 1.8 g. of 3-amino-4-benzyloxy-α-(N-benzyl-1-methyl-2-p-tolylethylaminomethyl)benzyl alcohol [A] and after adding to the solution 3 ml. of 5:3 anhydrous acetic acid-formic acid, the mixture was allowed to stand overnight. The residue obtained by concentrating the reaction mixture under a reduced pressure was dissolved in 20 ml. of methanol and after adding to the solution 2 ml. of water and 2 g. of sodium carbonate, the mixture was stirred for 3 hours at room temperature. The precipitates thus formed were recovered by filtration, washed with water and dried to provide 0.8 g. of white crystals of 4-benzyloxy-3-formamide-α-(N-benzyl-1-methyl-2-p-tolylethylaminomethyl)benzyl alcohol [A]. The product, on recrystallization from 4:1 n-hexane-benzene, melted at 125°–127° C.

EXAMPLE 15

In 50 ml. of ethanol there was dissolved 1.2 g. of 3-benzyloxyacetylamino-4-benzyloxy-α-[N-benzyl-N-(1-methyl-2-p-hydroxyphenylethyl)aminomethyl]benzyl alcohol and after adding to the solution 0.5 g. of 10% palladium carbon, the catalytic reduction was conducted at normal temperature and pressure until 137 ml. of hydrogen was absorbed. After filtering off the catalyst, the filtrate was concentrated under a reduced pressure to give 0.8 g. of white caramel-like 3-hydroxyacetylamino-4-hydroxy-α-[N-(1-methyl-2-p-hydroxyphenylethyl)aminomethyl]benzyl alcohol.

Nuclear magnetic resonance spectra (D$_6$-DMSO):

δ: 0.90 ppm. (d, 3H, >CH—CH$_3$), 3.98 ppm. (S, 2H,

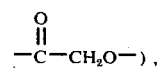

4.50 ppm. (m, 1H, >CH—OH).

EXAMPLE 16

In 30 ml. of methanol there was dissolved 800 mg. of 3-(N-acetyl-β-alanyl)amino-4-benzyloxy-α-[N-benzyl-N-(1-methyl-2-p-hydroxyphenylethyl)aminomethyl]-benzyl alcohol prepared by the procedure described in Reference Example 9 and after adding to the solution 50 mg. of 10% palladium carbon, the catalytic reduction was conducted at normal temperature and pressure until 65 ml. of hydrogen was absorbed. Then after filtering off the catalyst, the filtrate was concentrated under a reduced pressure to give 470 mg. of white carmel-like 3-(N-acetyl-β-alanyl)amino-4-hydroxy-α-[N-(1-methyl-2-p-hydroxyphenylethyl)aminomethyl]-benzyl alcohol.

Nuclear magnetic resonance spectra (D$_6$—DMSO):
δ: 0.90 ppm. (d, 3H,>CHCH$_3$), 1.80 ppm. (S, 3H, —COCH$_3$), 4.45 ppm. (m, 1H,>CHOH).

EXAMPLE 17

In 7 ml. of ethanol there was dissolved 0.7 g. of 4-benzyloxy-3-formylamino-α-[N-benzyl-N-(1-methyl-2-p-acetylaminophenylethyl)aminomethyl]benzyl alcohol and after adding to the solution 0.15 g. of 10% palladium carbon, the catalytic reduction was carried out at normal temperature and pressure until 61 ml. of hydrogen was absorbed. After filtering off the catalyst, the filtrate was concentrated under a reduced pressure to give 0.34 g. of a crystalline powder of 3-formylamino-4-hydroxy-α-[N-(1-methyl-2-p-acetylaminophenylethyl)aminomethyl]benzyl alcohol.

Nuclear magnetic resonance spectra (D$_6$-DMSO):
δ: 2.04 ppm. (S, 3H, H of the methyl group of p-acetylamino group), 8.30 ppm. (S, 1H, H of formyl group), 4.48 ppm. (m, 1H, H of the methine group at the root of hydroxyl group).

EXAMPLE 18

In 12 ml. of ethanol there was dissolved 1.2 g. of 4-benzyloxy-3-formylamino-α-[N-benzyl-N-(1-methyl-2-{3,4,5-trimethoxyphenyl}-ethyl)aminomethyl]benzyl alcohol prepared in Reference Example 10. After adding to the solution 0.2 g. of 10% palladium carbon, the catalytic reduction was conducted until 110 ml. of hydrogen was absorbed. The catalyst was then filtered off and the filtrate was concentrated under a reduced pressure to provide 0.7 g. of a crystalline powder of 3-formylamino-4-hydroxy-α-[N-(1-methyl-2-{3,4,5-trimethoxyphenyl}ethyl)aminomethyl]benzyl alcohol.

| Elemental analysis for C$_{21}$H$_{28}$N$_2$O$_6$: | | |
|---|---|---|
| | C(%) | H(%) | N(%) |
| Calculated: | 62.36 | 6.98 | 6.93 |
| Found: | 61.99 | 6.98 | 6.66 |

EXAMPLE 19

In 40 ml. of ethanol there was dissolved 2.2 g. of 4-benzyloxy-3-formylamino-α-[N-benzyl-N-(1-methyl-3-p-hydroxyphenylpropyl)-aminomethyl]benzyl alcohol prepared in Reference Example 10 and after adding to the solution 0.3 g. of 10% palladium carbon, the catalytic reduction was conducted at normal temperature and pressure until 195 ml. of hydrogen was absorbed. After filtering off the catalyst, the filtrate was concentrated under a reduced pressure to give 1.3 g. of crystalline powder of 3-formylamino-4-hydroxy-α-[N-(1-methyl-3-p-hydroxyphenylpropyl)aminomethyl] benzyl alcohol. When 0.60 g. of the product thus obtained and 0.102 g. of fumaric acid were dissolved in 95% ethanol and the solution was allowed to stand, a white crystal was formed, which was recovered by filtration to provide 0.55 g. of 3-formylamino-4-hydroxy-α-[N-(1-methyl-3-p-hydroxyphenylpropyl)aminomethyl] benzyl alcohol . ½ fumarate . monohydrate.

| Elemental analysis for C$_{21}$H$_{28}$N$_2$O$_7$: | | |
|---|---|---|
| | C(%) | H(%) | N(%) |
| Calculated: | 59.99 | 6.71 | 6.66 |
| Found: | 60.07 | 6.81 | 6.74 |

EXAMPLE 20

In 50 ml. of ethanol there was dissolved 1.62 g. of 3-formylamino-4-benzyloxy-α-[N-benzyl-N-(1-methyl-2-p-tolylethyl)aminomethyl]benzyl alcohol prepared by the procedure in Reference Example 10 and after adding to the solution 0.3 g. of 10% palladium carbon, the catalytic reduction was conducted at normal temperature and pressure until 154 ml. of hydrogen was absorbed. The catalyst was filtered off and after adding to the remaining ethanol solution 8 ml. of water, and 186 mg. of fumaric acid, the solvent was removed from the resultant solution under a reduced pressure. The residue was dissolved in ethanol and benzene was added to the solution until the solution became slightly turbid. When the system was allowed to stand in a refrigerator, 550 mg. of a white crystalline material was formed. The crystals were recovered and recrystallized from ethanol-benzene to give 3-formylamino-4-hydroxy-α-[N-(1-methyl-2-p-tolylethyl)aminomethyl]-benzyl alcohol . ½ fumarate . ½ hydrate melting at 132°–133° C. (decomposed).

| Elemental analysis for C$_{21}$H$_{26}$N$_2$O$_5$ . ½H$_2$O: | | |
|---|---|---|
| | C(%) | H(%) | N(%) |
| Calculated: | 63.78 | 6.88 | 7.08 |
| Found: | 63.99 | 6.70 | 6.82 |

EXAMPLE 21

In 10 ml. of ethanol there was dissolved 200 mg. of the 3-formylamino-4-benzyloxy-α-[N-benzyl-N-(1-ethyl-2-p-methoxyphenylethyl)aminomethyl]benzyl alcohol and after adding to the solution 50 mg. of 10% palladium carbon, the catalytic reduction was conducted at normal temperature and pressure until 31 ml. of hydrogen was absorbed. After filtering off the catalyst, the solvent was distilled off from the filtrate under a reduced pressure to give 100 mg. of a white caramel-like 3-formylamino-4-hydroxy-α-[N-(1-ethyl-2-p-methoxyphenylethyl)aminomethyl]benzyl alcohol.

Nuclear magnetic resonance spectra (D$_6$-DMSO): d
δ: 0.85 ppm. (3H, —CH$_2$CH$_3$), 1.25 ppm (2H, —CH$_2$CH$_3$), 4.47 ppm. (1H, —CHOH), 8.31 ppm.

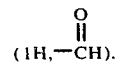

EXAMPLE 22

In 10 ml. of ethanol there was dissolved 0.52 g. of 3-formylamino-4-benzyloxy-α-[N-benzyl-N-(1-methyl-2-p-methoxyphenylethyl)aminomethyl]benzyl alcohol [A] prepared by the procedure described in Reference Example 11 d) and after adding to the solution 0.2 g. of 10% palladium carbon, the catalytic reduction was conducted at normal temperature and pressure until 48 ml. of hydrogen was absorbed. After filtering off the catalyst, the filtrate was concentrated under a reduced pressure to give 0.35 g. of a white crystalline powder of 3-formylamino-4-hydroxy-α-[N-(1-methyl-2-p-methoxyphenylethyl)aminomethyl]benzyl alcohol [A]. When 0.35 g. of the product was dissolved in 7 ml. of 95% ethanol together with 0.06 g. of fumaric acid and the solution was allowed to stand, crystals were formed. The crystals were recovered by filtration to provide 0.34 g. of white crystals of 3-formylamino-4-hydroxy-α-[N-(1-methyl-2-p-methoxyphenylethyl)aminomethyl]benzyl alcohol [A] . ½ fumarate melting at 138°–140° C. (decomposed).

| Elemental analysis for $C_{21}H_{28}N_2O_8 \cdot H_2O$: | | | |
|---|---|---|---|
| | C(%) | H(%) | N(%) |
| Calculated: | 59.99 | 6.71 | 6.66 |
| Found: | 59.63 | 6.65 | 6.71 |

EXAMPLE 23

In 30 ml. of ethanol there was dissolved 0.79 g. of 3-formylamino-4-benzyloxy-α-[N-benzyl-N-(1-methyl-2-methoxyphenylethyl)aminomethyl]benzyl alcohol [B] prepared by the procedure described in Reference Example 11 and after adding to the solution 0.2 g. of 10% palladium carbon, the catalytic reduction was conducted at normal temperature and pressure until 73 ml. of hydrogen was absorbed. Then, after filtering off the catalyst, the filtrate was concentrated under a reduced pressure to give 0.57 g. of a white powder of 3-formylamino-4-hydroxy-α-[N-(1-methyl-2-p-methoxyphenylethyl)aminomethyl]benzyl alcohol [B]. When 0.57 g. of the product was dissolved in 8 ml. of 95% ethanol together with 0.087 g. of fumaric acid and after adding to the solution 0.5 ml. of water, the resulting solution was allowed to stand, white crystals were formed. The crystals were recovered by filtration to provide 0.3 g. of 3-formylamino-4-hydroxy-α-[N-(1-methyl-2-p-methoxyphenylethyl)aminomethyl]benzyl alcohol [B] . ½-fumarate melting at 154°–155° C. (decomposed).

| Elemental analysis for $C_{21}H_{28}N_2O_6 \cdot \text{⅔}H_2O$: | | | |
|---|---|---|---|
| | C(%) | H(%) | N(%) |
| Calculated: | 60.89 | 6.65 | 6.76 |
| Found: | 60.94 | 6.69 | 6.77 |

EXAMPLE 24

In 40 ml. of ethanol there was dissolved 2.2 g. of 4-benzyloxy-3-formamide-α-[N-benzyl-3-(3,4-dimethoxyphenyl)-1-methylpropylaminomethyl]benzyl alcohol [A] and after adding to the solution 0.5 g. of 10% palladium carbon, the catalytic reduction was conducted at a normal temperature and pressure until 190 ml. of hydrogen was absorbed. After filtering off the catalyst, the filtrate was concentrated under a reduced pressure to provide 1.4 g. of a white powder of 3-formamide-4-hydroxy-α-[3-(3,4-dimethoxyphenyl)-1-methylpropylaminomethyl]benzyl alcohol.

When 750 mg. of the product was dissolved in 15 ml. of 90% isopropanol together with 120 mg. of fumaric acid and the solution was allowed to stand, white crystals formed. The crystals thus formed were recovered by filtration, whereby 700 mg. of 3-formamide-4-hydroxy-α-[3-(3,4-dimethoxyphenyl)-1-methylpropylaminomethyl]benzyl alcohol [A] ½fumarate melting at 134°–136° C (decomposed) was obtained.

Nuclear magnetic resonance spectra ($D_6$-DMSO)
δ: 1.22 ppm (3H, d, >CH—C$\underline{H}_3$), 3.65, 3.67 ppm (6H, 2-OC$\underline{H}_3$), 4.79 ppm (1H, m, >C$\underline{H}$—OH), 8.33 ppm (1H, s, >N-C$\underline{H}$O)

EXAMPLE 25

In 20 ml. of ethanol there was suspended 1 g. of 4-benzyloxy-3-formamide-α-[N-benzyl-N-(α,α-dimethylphenethyl)aminomethyl]benzyl alcohol and after adding to the suspension 3 g. of 10% palladium carbon, the catalytic reduction was conducted at a normal temperature and pressure until 95 ml. of hydrogen was absorbed. After filtering off the catalyst, the filtrate was concentrated under a reduced pressure to provide 0.63 g. of a white powder of 3-formamide-4-hydroxy-α(α,α-dimethylphenethylaminomethyl)benzyl alcohol.

When 550 mg. of the product was dissolved in 10 ml. of 90% ethanol together with 110 mg. of fumaric acid and the solution was allowed to stand overnight, white crystals formed. The crystals were recovered by filtration to provide 550 mg. of 3-formamide-4-hydroxy-α-(α,α-dimethylphenethylaminomethyl)benzyl alcohol . ½-fumarate monohydrate melting at 143°–145° C.

| Elemental analysis for $C_{21}H_{26}N_2O_5 \cdot H_2O$: | | | |
|---|---|---|---|
| | C(%) | H(%) | N(%) |
| Calculated: | 62.36 | 6.98 | 6.93 |
| Found: | 62.79 | 7.01 | 6.71 |

Nuclear magnetic resonance spectra (CDCl$_3$)
δ: 2.32 ppm (3H, s,

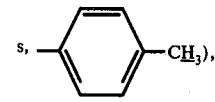

3.49, 3.89 ppm. (2H, AB-q,

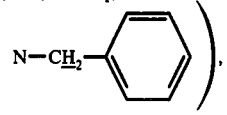

4.52 ppm (1H, m,>C$\underline{H}$-OH), 5.05 ppm (2H, s,

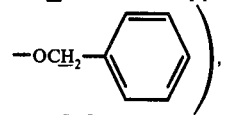

8.36 ppm (1H, s,>N-C$\underline{H}$O)

By treating with 1.0 g. of 3-amino-4-benzyloxy-α-(N-benzyl-1-methyl-2-p-tolylethylaminomethyl)benzyl alcohol [B] in the same manner as above, 0.9 g. of white crystals of 4-benzyloxy-3-formamide-α-(N-benzyl-1-methyl-2-p-tolylethylaminomethyl)benzyl alcohol [B] were obtained melting at 116°–119° C.

Nuclear magnetic resonance spectra
δ: 2.30 ppm (3H, s,

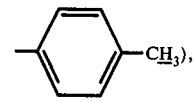

3.77 ppm (2H, d, >N—C$\underline{H}_2$—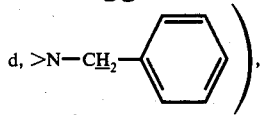, 2.42 ppm (1H, m, >C$\underline{H}$—CH), 5.05 ppm (2H, s, —O—C$\underline{H}_2$—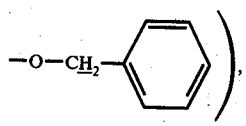, 8.36 ppm (1H, s, N—C$\underline{H}$O)

EXAMPLE 26

In 20 ml. of ethanol there was dissolved 1.2 g. of 4-benzyloxy-3-formamide- -(N-benzyl-1-methyl-3-p-tolylpropylaminomethyl)benzyl alcohol and after adding to the solution 0.3 g. of 10% palladium carbon, the catalyst reduction was conducted at a normal temperature and pressure until 115 ml. of hydrogen was absorbed. After filtering off the catalyst, the filtrate was concentrated under a reduced pressure to provide 0.8 g. of a white powder of 3-formamide-4-hydroxy- -(1-methyl-3-p-tolylpropylaminomethyl)benzyl alcohol [A].

When 800 mg. of the product was dissolved in 20 ml. of 90% isopropanol together with 130 mg. of fumaric acid and the solution was allowed to stand, 700 mg. of white crystals of 3-formamide-4-hydroxy- -(1-methyl-3-p-tolylpropylaminomethyl)benzyl alcohol [A] fumarate were obtained melting at 110 –113 C.

Nuclear magnetic resonance spectra (D -DMSO) : 1.18 ppm (3H, d, CH-C$\underline{H}$ ), 2.28 ppm (3H, s, —CH ) 4.72 ppm (1H, m, C$\underline{H}$-OH), 8.34 ppm (1H, s, N-C$\underline{H}$O) 6.52 ppm (1H, s,

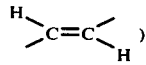

EXAMPLE 27

In 40 ml. of ethanol there was dissolved 2.3 g. of 4-benzyloxy-3-formamide- -(N-benzyl- -methyl-phenethylaminomethyl)benzyl alcohol [A] and after adding to the solution 0.15 g. of 10% palladium carbon, the catalytic reduction was conducted at a normal temperature and pressure until 220 ml. of hydrogen was absorbed. After filtering off the catalyst, 270 mg. of fumaric acid was dissolved in the filtrate and the solvent was distilled off under reduced pressure. When 20 ml. of isopropanol was added to the residue thus obtained and the solution was allowed to stand, followed by adding 5 ml. of water, crystals were formed. The crystals were recovered by filtration to provide 1.2 g. of white crystals of 3-formamide-4-hydroxy- -( -methyl-phenethylaminomethyl)benzyl alcohol [A] . fumarate monohydrate melting at 115 –117 C (decomposed).

| Elemental analysis for C H N O . H O | | |
|---|---|---|
| C(%) | H(%) | N(%) |
| Calculated: 61.53 | 6.71 | 7.17 |
| Found: 61.46 | 6.65 | 7.13 |

EXAMPLE 28

In 50 ml. of ethanol there was dissolved 1.09 g. of 4-benzyloxy-3-formamide- -(N-benzyl-3-p-methoxyphenyl-1-methylpropylaminomethyl)benzyl alcohol [A] and after adding to the solution 0.5 g. of 10% palladium carbon, the catalytic reduction was conducted at a normal temperature and pressure until 97 ml. of hydrogen was absorbed. After filtering off the catalyst, the filtrate was concentrated under a reduction pressure to provide 0.52 g. of white powdery crystals of 3-formamide-4-hydroxy- -(3-p-methoxyphenyl-1-methylpropylaminomethyl)benzyl alcohol [A]. When 0.5 g. of the product was dissolved in 10 ml. of ethanol together with 0.08 g. of fumaric acid and the solution was allowed to stand in an ice-cooled room followed by adding 20 ml. of benzene, crystals were formed. The crystals were recovered by filtration to provide 0.3 g. of white crystals of 3-formamide-4-hydroxy- -(3-p-methoxyphenyl-1-methyl-propylaminomethyl)benzyl alcohol [A] . fumarate melting at 143 –145 C (decomposed).

| Elemental analysis for C H N O (decomposed) | | |
|---|---|---|
| C(%) | H(%) | N(%) |
| Calculated: 63.45 | 6.78 | 6.73 |
| Found: 63.72 | 6.66 | 6.68 |

EXAMPLE 29

In 50 ml. of ethanol there was dissolved 2.15 g. of 4-benzyloxy-3-formamide- -(N-benzyl- -methyl-3,4-dimethoxyphenethylaminomethyl)benzyl alcohol and after adding to the solution 0.3 g. of 10% palladium carbon, the catalytic reduction was conducted at a normal temperature and pressure until 194 ml. of hydrogen was absorbed. After filtering off the catalyst, 0.2 g. of fumaric acid was dissolved in the filtrate, and the solution was concentrated under a reduced pressure to provide 1.5 g. of 3-formamide-4-hydroxy- -( -methyl-3,4-dimethoxyphenethylaminomethyl)benzyl alcohol fumarate.

Nuclear magnetic resonance spectra (D -DMSO) δ: 1.01 ppm (3H, d, >CH—C$\underline{H}_3$) 3.71 ppm (6H, s,

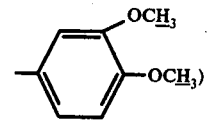

8.29 ppm (1H, s, -C$\underline{H}$O)

EXAMPLE 30

In 15 ml. of ethanol there was suspended 570 mg. of 4-benzyloxy-3-formamide-α-(N-benzyl-1-methyl-2-p-tolylethylaminomethyl)benzyl alcohol [A] and after adding to the suspension 0.3 g. of 10% palladium carbon, the catalytic reduction was conducted at a normal temperature and pressure until 54 ml. of hydrogen was absorbed. After filtering off the catalyst, the filtrate was concentrated under a reduced pressure to provide 360 mg. of a white powder of 3-formamide-4-hydroxy-α-(1-methyl-2-p-tolylethylaminomethyl)benzyl alcohol [A]. When 330 mg. of the product was dissolved in 10 ml. of 80% isopropanol together with 60 mg. of fumaric acid and the solution was allowed to stand, white crystals were formed. The crystals were recovered by filtration to provide 320 mg. of 3-formamide-4-hydroxy-α-(1-methyl-2-p-tolylethylaminomethyl)benzyl alcohol [A] ½fumarate monohydrate melting at 126°–128° C.

| Elemental analysis for C₂₁H₂₆N₂O₅ . H₂O | | | |
|---|---|---|---|
| | C(%) | H(%) | N(%) |
| Calculated: | 62.36 | 6.98 | 6.93 |
| Found: | 62.41 | 6.74 | 6.94 |

EXAMPLE 31

By treating with 570 mg. of 4-benzyloxy-3-formamide-α-(N-benzyl-1-methyl-2-p-tolylethylaminomethyl)benzyl alcohol [B] in the same manner as in Example 30, 270 mg. of 3-formamide-4-hydroxyα-(1-methyl-2-p-tolylethylaminomethyl)benzyl alcohol [B] ½fumarate were obtained melting at 127°–128° C.

| Elemental analysis for C₂₁H₂₆N₂O₅ | | | |
|---|---|---|---|
| | C(%) | H(%) | N(%) |
| Calculated: | 62.36 | 6.98 | 6.93 |
| Found: | 62.51 | 6.81 | 6.98 |

EXAMPLE 32

In 10 ml. of ethanol there was suspended 0.52 g. of 4-benzyloxy-3-formamide-α-(N-benzyl-3-p-hydroxyphenyl-1-methylpropylaminomethyl)benzyl alcohol [A] and after adding to the suspension 0.3 g. of 10% palladium carbon, the catalytic reduction was conducted at a normal temperature and pressure until 48 ml. of hydrogen was absorbed. After filtering off the catalyst, the filtrate was concentrated under a reduced pressure to provide 0.32 g. of a white powder of 3-formamide-4-hydroxy-α-(3-p-hydroxyphenyl-1-methylpropylaminomethyl)benzyl alcohol [A].

When 320 mg. of the product was dissolved in 10 ml. of 90% isopropanol together with 55 mg. of fumaric acid and the solution was allowed to stand, white crystals formed. The crystals were recovered by filtration to provide 310 mg. of 3-formamide-4-hydroxy-α-(3-p-hydroxyphenyl-1-methylpropylaminomethyl)benzyl alcohol [A] ½ fumarate monohydrate melting at 144°–146° C (decomposed).

| Elemental analysis for C₂₁H₂₆N₂O₆ . H₂O | | | |
|---|---|---|---|
| | C(%) | H(%) | N(%) |
| Calculated: | 59.99 | 6.71 | 6.66 |
| Found: | 60.34 | 6.69 | 6.56 |

EXAMPLE 33 (TABLET)

Formulation:

| | |
|---|---|
| 3-Formylamino-4-hydroxy-α-[N-(1-methyl-2-p-hydroxyphenyl-ethyl)aminomethyl]benzyl alcohol [A] ½ fumarate (Example 8) | 100 mg. |
| Lactose | 100.0 g |
| Starch | 35.0 g |
| Talc | 5.0 g |

From the above formula 1,000 tablets were prepared by a conventional procedure. Each tablet had a diameter of 7 mm. and where necessary, a coating was applied thereto.

EXAMPLE 34 (INJECTABLE)

Formulation:

| | |
|---|---|
| 3-Formylamino-4-hydroxy-α-[N-(1-methyl-2-p-hydroxyphenyl-ethyl)aminomethyl]benzyl alcohol [A] ½ fumarate (Example 8) | 5 mg |
| Sodium chloride | 8.5 g |
| Citric acid | 1.0 g |
| Water to make | 1,000 ml. |
| | pH 4.0 – 6.0 |

From the above formula, 1,000 injection ampoules each containing 1 ml. were prepared. The injection was prepared by dissolving the above components in water, adjusting the pH, sterilizing by filtration, and poured in an ampoule followed by seal.

EXAMPLE 35 (INJECTION)

Formula:

| | |
|---|---|
| 3-Formylamino-4-hydroxy-α-[N-(1-methyl-2-p-hydroxyphenyl-ethyl)aminomethyl]benzyl alcohol [A] ½ fumarate (Example 8) | 5 mg |
| Mannitol | 56 g |
| Acetic acid | 1.0 g |
| Water to make | 1,000 ml. |
| | pH 4.0 – 6.0 |

From the above formula 1,000 injection ampoules each containing 1 ml. were prepared. The injectable was prepared by dissolving the above components in water, adjusting the pH, sterilizing by filtration, pouring into an ampoule followed by sealing.

What is claimed is:

1. A compound selected from the group consisting of 3-formylamino-4-hydroxy-α-[N-(1-methyl-2-p-methoxyphenylethyl)aminomethyl]benzyl alcohol of the formula:

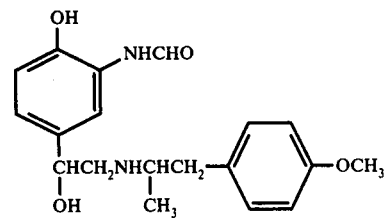

and the pharmacologically acceptable non-toxic acid addition salts thereof.

2. A compound according to claim 1 which is 3-formylamino-4-hydroxy-α-[N-(1-methyl-2-p-methoxyphenylethyl)aminomethyl]benzyl alcohol ½ fumarate.

3. A compound according to claim 1 which is 3-formylamino-4-hydroxy-α-[N-(1-methyl-2-p-methoxyphenylethyl)aminomethyl]benzyl alcohol ½ fumarate showing melting point (decomposition) of 138°–140° C.

4. A compound according to claim 1 which is 3-formylamino-4-hydroxy-α-[N-(1-methyl-2-p-methoxyphenylethyl)aminomethyl]-benzyl alcohol of ½ fumarate showing melting point (decomposition) of 154°–155° C.

* * * * *

UNITED STATES PATENT OFFICE
CERTIFICATE OF CORRECTION

Patent No. 3,994,974  Dated November 30, 1976

Inventor(s) Masuo Murakami, et al

It is certified that error appears in the above-identified patent and that said Letters Patent are hereby corrected as shown below:

Column 1, line 63: "bronchlodilating" should read --bronchodilating--.

Column 18, line 34: "catalyst" should read --catalytic--.

Column 19, line 68: "151°-153° should read --151.8-153°C--.
Column 23, line 55: After "acetylaminophenylethyl" cancel hyphen
Column 24, line 46: "methoxyphenyletyl" should read --methoxyphenylethyl--.

Column 25, line 3: "200 1ml." should read --200 ml.--.

line 11: "concentraed" should read --concentrated--.

line 22: "concentraed" should read --concentrated--.

line 28: "carmel" should read --caramel--.

line 29: "N-(1-methyl-2-methoxyphenylethyl)aminomethyl]-" should read -- N-(1-methyl-2-p-methoxyphenylethyl)aminomethyl]- --.

Column 26, line 22: "the" should read --a--.

Column 27, line 64: "0.97 ppm" should read -- : 0.97 ppm --.

Column 28, line 66: "(1H,s--C$\underline{H}$O)" should read --(1H, s, -C$\underline{H}$O)--

UNITED STATES PATENT OFFICE
CERTIFICATE OF CORRECTION

Patent No. 3,994,974  Dated November 30, 1976

Inventor(s) Masuo Murakami, et al

It is certified that error appears in the above-identified patent and that said Letters Patent are hereby corrected as shown below:

Column 33, line 27: "2-methoxyphenylethyl)" should read
-- 2-p-methoxyphenylethyl) --.

Column 35, line 15: "4-benzyloxy-3-formamide- -(N-" should read
-- 4-benzyloxy-3-formamide- α-(N- --.

line 22: "3-formamide-4-hydroxy- -(1-" should read
-- 3-formamide-4-hydroxy- α-(1- --.

line 28: "3-formamide-4-hydroxy- -(1-methyl-" should read -- 3-formamide-4-hydroxy- α-(1-methyl- --.

line 30: "fumarate" should read --1/2 fumarate--.

line 31: "(D-DMSO)" should read --($D_6$-DMSO)--.

line 32: " : 1.18 ppm" should read -- $\delta$: 1.8 ppm --.

line 32: "(3H, d, CH-C$\underline{H}$ )" should read
--(3H, d, >CH-C$\underline{H}_3$) --.

line 33: " -C$\underline{H}$ )4.72 ppm (1H, m, C$\underline{H}$-OH)" should read -- -C$\underline{H}_3$)4.72 ppm (1H, m, >C$\underline{H}$-OH) --.

line 34: "N-C$\underline{H}$O)" should read -- >N-C$\underline{H}$O) --.

UNITED STATES PATENT OFFICE
CERTIFICATE OF CORRECTION

Patent No. 3,994,974          Dated November 30, 1976

Inventor(s) Masuo Murakami, et al

It is certified that error appears in the above-identified patent and that said Letters Patent are hereby corrected as shown below:

Column 35, line 35: " 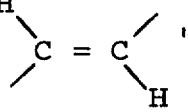 " should read -- 1/2 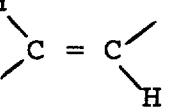 --

Column 35, line 43: "4-benzyloxy-3-formamide- -(N-benzyl- -methyl-" should read -- 4-benzyloxy-3-formamide- α-(N-benzyl-α-methyl- --.

line 55: "3-formamide-4-hydroxy- -( -methyl-" should read -- 3-formamide-4-hydroxy- α-(α-methyl- --.

line 56: "alcohol [A] . fuma-" should read --alcohol [A] . 1/2fuma- --.

line 57: "115-117 C" should read --115-117°C--.

line 61: "C H N O . H O" should read --$C_{20}H_{24}N_2O_5 \cdot H_2O$--.

line 68: "4-benzyloxy-3-formamide- -(N-benzyl-3-p-methox-" should read -- 4-benzyloxy-3-formamide- α-(N-benzyl-3-p-methox- --.

Column 36, lines 6 and 7: "reduction" should read --reduced--.

line 8: "3-formamide-4-hydroxy- -(3-methoxy" should read -- 3-formamide-4-hydroxy- α-(3-p-methoxy --.

UNITED STATES PATENT OFFICE
CERTIFICATE OF CORRECTION

Patent No. 3,994,974      Dated November 30, 1976

Inventor(s) Masuo Murakami, et al

It is certified that error appears in the above-identified patent and that said Letters Patent are hereby corrected as shown below:

Column 36, line 17: "hydroxy- -(3-p-methoxyphenyl-1-methyl-" should read --hydroxy-$\alpha$-(3-p-methoxyphenyl-1-methyl- --.

line 18: "alcohol[A] . fumarate" should read --alcohol[A]. 1/2fumarate--.

line 19: "143-145 C" should read --143-145°C--.

line 21: "C H N O" should read --$C_{22}H_{28}N_2O_6$--.

line 30: "4-benzyloxy-3-formamide- -(N-benzyl- -methyl-" should read -- 4-benzyloxy-3-formamide-$\alpha$-(N-benzyl-$\alpha$-methyl- --.

line 39: "3-formamide-4-hydroxy- -( -" should read --3-formamide-4-hydroxy-$\alpha$-($\alpha$- --.

line 41: "alcohol fumarate" should read -- alcohol 1/2fumarate--.

line 42: "(D -DMSO)" should read -- ($D_6$-DMSO) --.

*Signed and Sealed this*

*Thirteenth* Day of *September 1977*

[SEAL]

Attest:

RUTH C. MASON          LUTRELLE F. PARKER
*Attesting Officer*      *Acting Commissioner of Patents and Trademarks*